United States Patent [19]

Fujita et al.

[11] Patent Number: 5,609,791

[45] Date of Patent: *Mar. 11, 1997

[54] DIENE DERIVATIVE

[75] Inventors: Atsuko Fujita; Shuichi Matsui; Yuichi Onji; Makoto Ushioda; Yasuyuki Goto, all of Chiba-ken, Japan

[73] Assignee: Chisso Corporation, Ohsaka-fu, Japan

[ * ] Notice: The term of this patent shall not extend beyond the expiration date of Pat. No. 5,449,810.

[21] Appl. No.: 450,805

[22] Filed: May 25, 1995

Related U.S. Application Data

[62] Division of Ser. No. 41,184, Apr. 1, 1993, Pat. No. 5,449,810.

[30] Foreign Application Priority Data

Apr. 3, 1992 [JP] Japan .................................... 4-82209

[51] Int. Cl.⁶ ............................................ C07C 255/50
[52] U.S. Cl. ..................... 252/299.63; 252/299.66; 558/411; 568/647; 570/128; 585/25
[58] Field of Search .................... 585/25; 570/128; 568/647; 558/411; 252/299.66, 299.63

[56] References Cited

U.S. PATENT DOCUMENTS

| | | | |
|---|---|---|---|
| 4,621,901 | 11/1986 | Petrzilka et al. | 558/426 X |
| 4,676,604 | 6/1987 | Petrzilka | 558/411 X |
| 4,707,295 | 11/1987 | Pohl et al. | 558/426 X |
| 4,710,315 | 12/1987 | Schad et al. | 558/423 X |
| 4,770,503 | 9/1988 | Buchecker et al. | 558/411 X |
| 4,784,471 | 11/1988 | Wachtler et al. | 558/425 X |
| 4,846,998 | 7/1989 | Pohl et al. | 558/425 X |
| 4,879,061 | 11/1989 | Ferrato et al. | 558/411 X |
| 4,985,583 | 1/1991 | Eidenschink et al. | 558/426 X |

FOREIGN PATENT DOCUMENTS

| | | |
|---|---|---|
| 0122389 | 10/1985 | European Pat. Off. . |
| 0331091 | 9/1989 | European Pat. Off. . |
| 0458176 | 11/1991 | European Pat. Off. . |
| 2822504 | 11/1979 | Germany . |
| 3223637 | 1/1983 | Germany . |
| 0118752 | 7/1984 | Japan . |

OTHER PUBLICATIONS

Database WPI, Section Ch, Week 9032, Derwent Publications, Ltd., London, GB; Class E10, AN 90–241464 & JP–A–2 160 756 (Adeka–Argus Chem KK) 20 Jun. 1990.

*Primary Examiner*—Robert Gerstl
*Attorney, Agent, or Firm*—Wenderoth, Lind & Ponack

[57] ABSTRACT

A novel liquid crystal material having a carbon chain containing a conjugated diene as a terminal substituent of the molecule and exhibiting superior characteristics is provided, which is a diene derivative expressed by the formula (I)

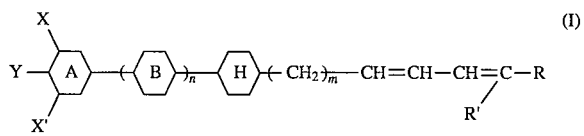

wherein R and R' each independently represent 1–5C alkyl; A and B each independently represent 1,4-cyclohexylene or 1,4-phenylene; n is 0 or 1; m is an integer of 0 to 2; X and X' each independently represent H atom or F atom when A is 1,4-phenylene or represent H atom when A is 1,4-cyclohexylene; Y is alkyl, halogen or CN, alkoxy, methyl group substituted by 1–3 halogen atoms or trihaloalkoxy when A is 1,4-phenylene, or represent alkyl, alkoxy, methyl group substituted by 1–3 halogen atoms or trihaloalkoxy when A is 1,4-cyclohexylene; and R and R' are not simultaneously alkyl chain of 4 or more carbon atoms.

The compound of the present invention has a generally usable viscosity and a high NI point and a high elastic constant ratio; hence the liquid crystal composition, particularly the liquid crystal composition for STN, containing the compound of the present invention exhibits improved characteristics as compared with the conventional ones.

7 Claims, No Drawings

DIENE DERIVATIVE

This is a divisional application of Ser. No. 08/041,184 filed Apr. 1, 1993, now U.S. Pat. No. 5,449,810.

BACKGROUND OF THE INVENTION

1. Field of the Invention

This invention relates to a diene derivative useful for liquid crystal materials. More particularly, it relates to a liquid crystalline compound containing a conjugated diene inside its molecule and a liquid crystal composition containing the same.

2. Description of the Related Art

Display elements making use of liquid crystals have been broadly utilized for clocks, electronic computers, etc. These liquid crystal display elements utilize the optical anisotropy and dielectric anisotropy of liquid crystal substances. Liquid crystal phases include a nematic liquid crystal phase, smectic liquid crystal phase and cholesteric liquid crystal phase. Among these phases, display elements utilizing nematic liquid crystal have been most broadly practically used. Further, display modes applied to the liquid crystal display includes TN (twisted nematic) mode, DS (dynamic scattering) mode, guest-host mode, DAP mode, etc. Many liquid crystalline compounds including those at a studying stage have been know, but at present, there is no single substance which is sealed in a display element and used.

This is because while liquid crystal substances expected to be used as display elements are preferred to be those which exhibit liquid crystal phase within a temperature range as possible as broad around a room temperature at which they are most often used as display elements, in the natural fields, and further they should be sufficiently stable to environmental factors used and have sufficient physical properties for driving the display element, no single substance satisfying these conditions has not yet been found. Thus, at present, compositions having such characteristics have been prepared by mixing several kinds of liquid crystal materials or further mixing non-liquid crystalline compounds therewith, and have been practically used as liquid crystalline materials. Further, these liquid crystal compositions are required to be stable to moisture, light, heat, air, etc. usually present under the environment where they are used. Further, the compositions are required to be stable to electric field and electromagnetic irradiation, and further the liquid crystalline compounds to be mixed are required to be chemically stable to one another under the environment where they are used. Further, the values of various physical properties such as optical anisotropy value, dielectric anisotropy value, conductance value, etc. are required to be suitable values corresponding to a display mode and a shape of element. In particular, an importance of a substance having a low optical anisotropy value as a material for liquid crystal display element of thin film transistor (TFT) mode and a compound having a large elastic constant ratio ($K_3/K_1$) as a material for super twisted nematic (STN) mode has been recently increasing. In order to correspond to such requirements, single substance liquid crystalline compounds having various characteristics have been developed, and as a compound for improving particularly the values of the viscosity and elastic constant ratio, compounds having a carbon chain having an unsaturated bond at the terminal part of the molecule, as mentioned below, has been found (Japanese patent application laid-open No. Sho 59-176221). Further, as a compound having a rigid molecular structure, a compound having a dienyl group, as mentioned below, has been developed (Japanese patent publication No. Hei 2-207056). However, the compound disclosed in the latter publication has been limited to that having the core part which is most important for exhibiting liquid crystallinity ether-bonded to the dienyl group. Further, as to the core part, too, the compound has been limited to that having 4-(4-phenyl)ethynylphenyl (tolan) structure. Thus, the compound has a high viscosity and is poor in utility, as a liquid crystalline material.

Thus, it has been required to develop a new material which can solve these problems.

A compound disclosed in Japanese patent application laid-open No. Sho 59-176221:

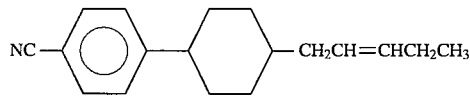

A compound disclosed in Japanese patent publication No. Hei 2-207056:

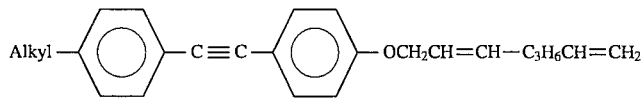

The object of the present invention is to provide a liquid crystalline compound having improved values of the viscosity and the elastic constant ratio.

The present inventors have made extensive research in order to solve the above-mentioned problems, and as a result, have found a compound having a novel structure and having improved characteristics as compared with generally known liquid crystalline compounds, and have completed the present invention.

The present invention is characterized by a diene derivative expressed by the formula (I)

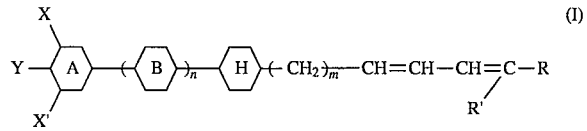

wherein R and R' each independently represent a hydrogen atom or an alkyl group of 1 to 5 carbon atoms; A and B each independently represent 1,4-cyclohexylene or 1,4-phenylene; n represents 0 or 1; m represents an integer of 0 to 2; X and X' each independently represent a hydrogen atom or a fluorine atom when A represents 1,4-phenylene, and a hydrogen atom when A represents 1,4-cyclohexylene; and Y represents an alkyl group, a halogen atom, a cyano group, an alkoxy group, a methyl group substituted by 1 to 3 halogen atoms or a trihaloalkoxy group when A represents 1,4-phenylene, or an alkyl group, an alkoxy group, a methyl group substituted by 1 to 3 halogen atoms or a trihaloalkoxy group when A represents 1,4-cyclohexylene group; and R and R' do not represent simultaneously an alkyl group of 4 or more carbon atoms.

DETAILED DESCRIPTION OF PREFERRED EMBODIMENTS

The compound of the present invention has a conjugated butadiene chain at the terminal part of the compound and this chain is bonded to the core part bia C—C bond, whereby the elastic constant ratio is as high as have never seen before and the mesomorphic temperature range is broadened to a large extent as compared with those of the corresponding compounds having a monoene structure. Further, the compound of the present invention is structurally rigid, and nevertheless has a low viscosity and has a suitable optical anisotropy value. Further, the compound of the present invention is sufficiently stable under the environment of its use as liquid crystal element, and also cause no degradation under conditions of electromagnetic irradiation, voltage impression, etc. Further, when the compound of the present invention is used as a component for liquid crystal composition, it has a superior compativility with other liquid crystalline materials, whereby it is possible to compose a new liquid crystal display element having useful characteristics. Further, the compound of the present invention can vary its characteristics by varying its ring structures and the substituents on the rings thereof.

Among the compounds of the present invention, preferable ones are exemplified as follows:

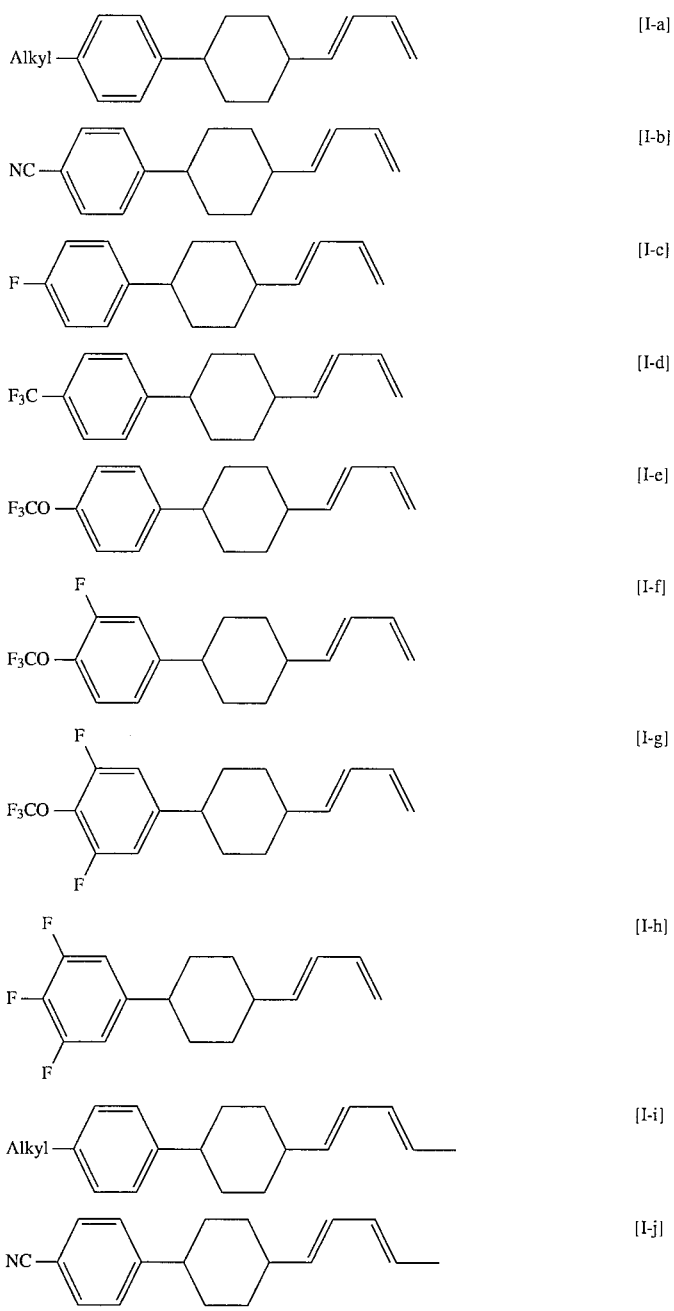

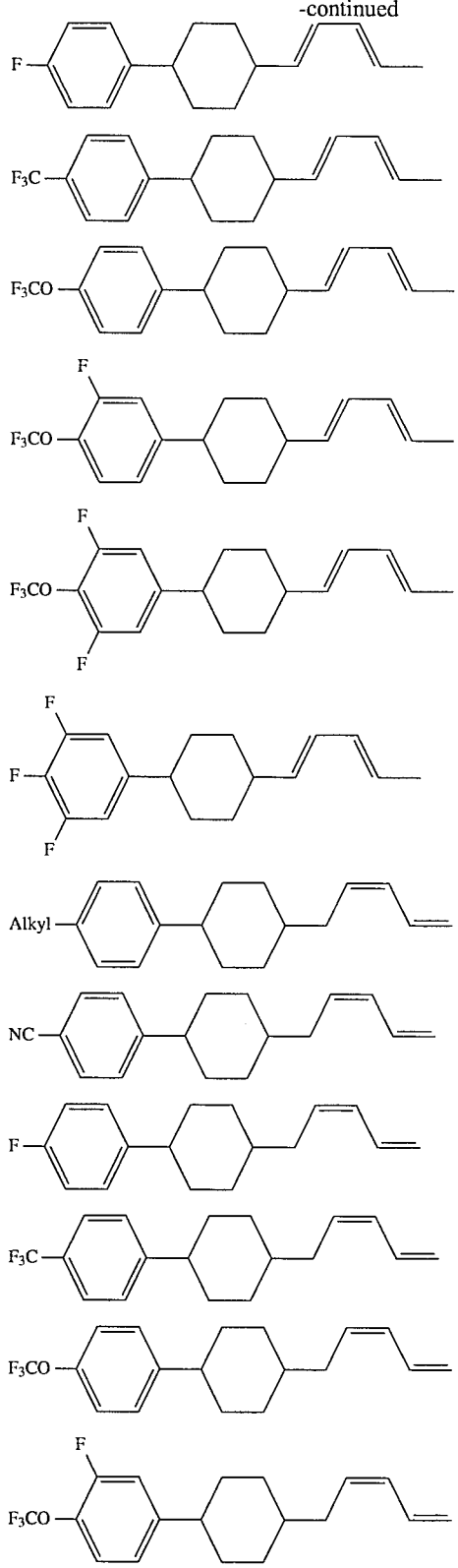

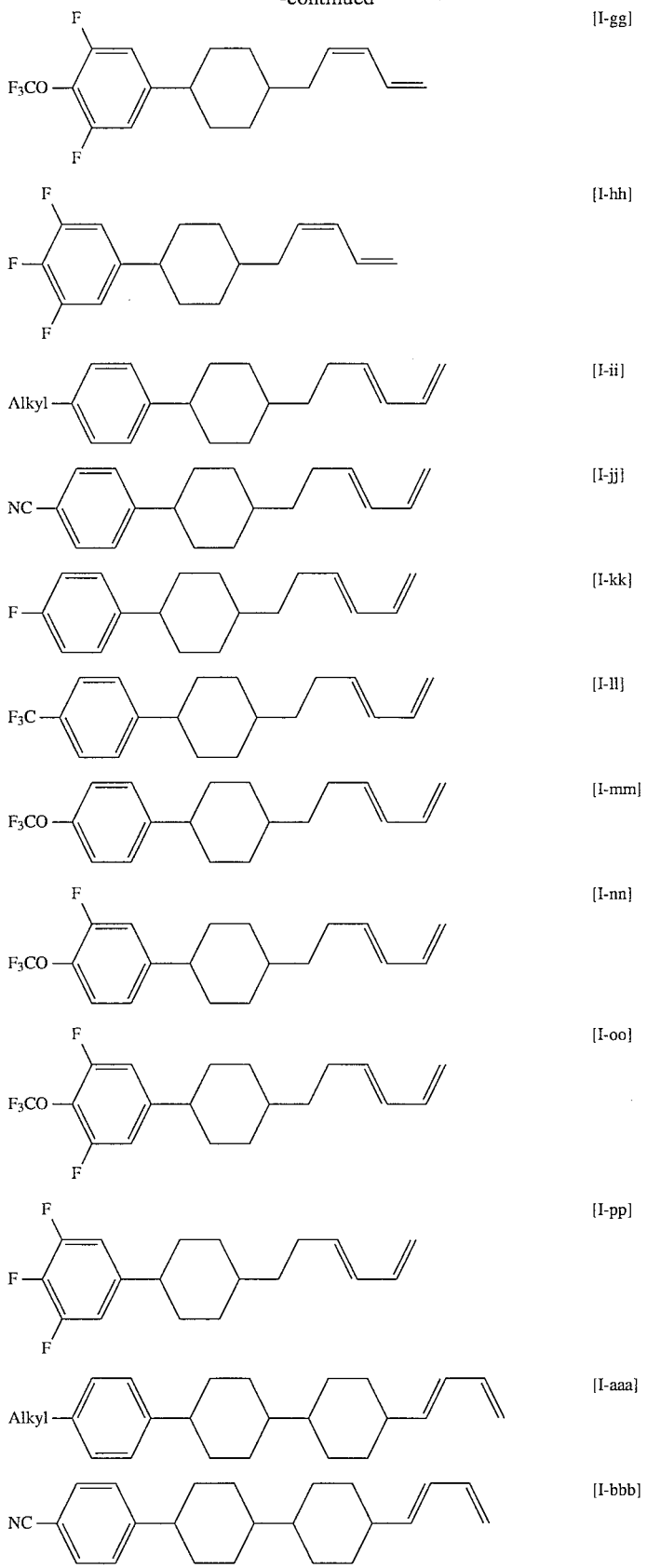

-continued
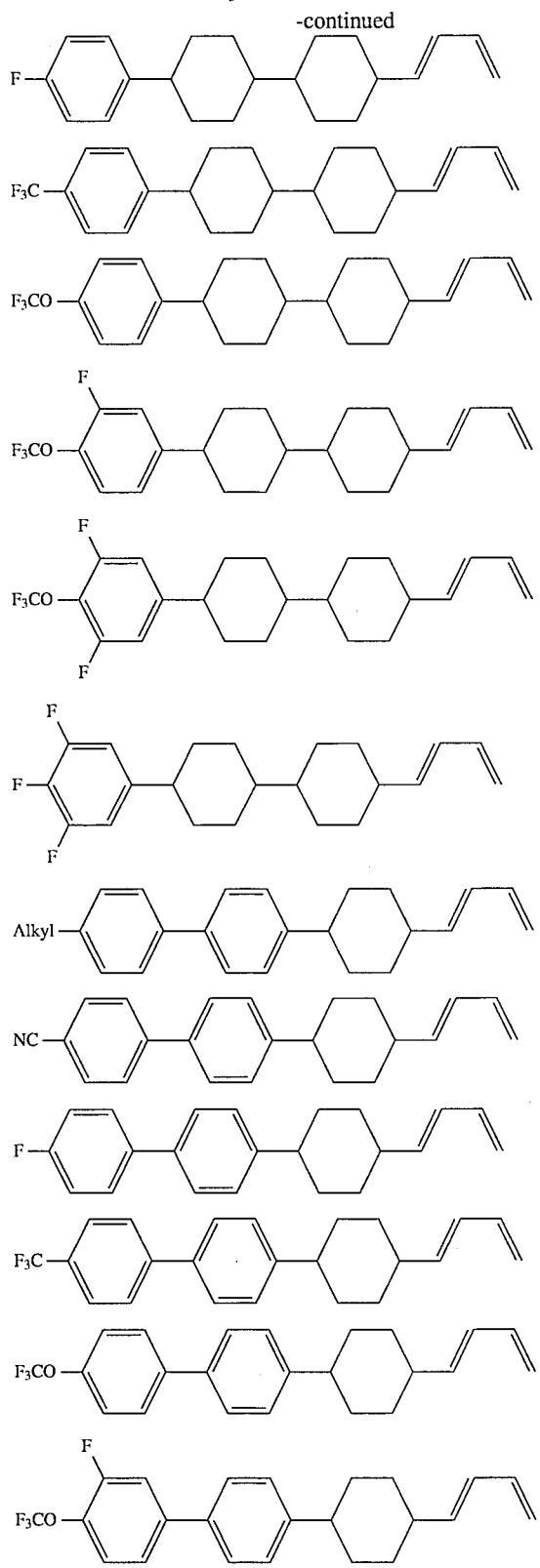

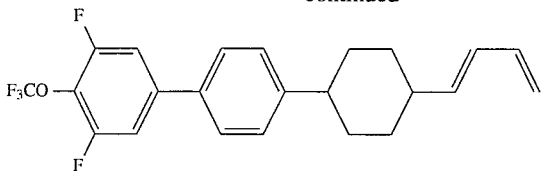
[I-ooo]

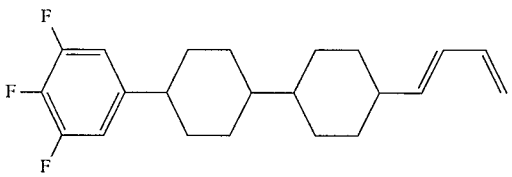
[I-ppp]

Among these compounds, those of I-b, I-j, I-bb, I-jj, I-bbb and I-jjj having a cyano group as Y (Y=CN) afford large dipole moments, and those of I-d, I-l, I-dd, I-ll, I-ddd and I-lll having a trifluoromethyl group reduce the viscosity and afford a polarizability; hence either of the compounds are preferred. Further, among the compounds of the present invention, even in the case of those having two six-membered rings in the molecule i.e. the so-called two-rings compounds, it is possible to establish the liquid crystal temperature range in the vicinity of a room temperature, and those having three six-membered rings in the molecule i.e. the so-called three-rings compounds are preferred in that they have extraordinarily large elastic constant ratios and broaden a liquid crystal range.

Among the compounds of the present invention, those expressed by the formula (I) wherein Y represents an alkyl group of 2 to 5 carbons are preferred in that they broaden a liquid crystal range; those of the formula (I) wherein Y represents a fluorine atom as the halogen atom are preferred in that the viscosity is reduced; those of the formula (I) wherein Y represents a methyl group substituted by 1 to 3 fluorine atoms are preferred as those substituted by halogen atoms, and further, among these, those substituted by 2 or 3 fluorine atoms are preferred in that stability can be retained. As to trihaloalkyls, trichloroalkyl and trifluoroalkyl are preferred in that viscosity is retained at a lower value and a suitable dielectric anisotropy value is obtained. Further, as R and R', a linear alkyl chain group of carbon atoms within (5-m) is preferred in that a liquid crystal range is broadened.

Further, the carbon chain containing a dienyl structure positioned at the terminal part of the molecule of the compound of the present invention has some steric isomers originated from the double bond. Namely, in the case where R and R' are both not hydrogen atoms and not equal alkyl groups, there are 4 kinds of isomers of E, E; E, Z; Z, Z and Z, E, and in the case where R and R' are both hydrogen atoms or equal alkyl groups, there are 2 kinds of isomers of E and Z. Among these steric forms of isomers, E, E form in the case where m represents 0 or 2 and R and R' are both not hydrogens atom and not equal alkyls; E form in the case where R and R' are both hydrogen atom, Z, Z form in the case where m is 1 and R and R' are both not hydrogen atoms and not equal alkyl groups; and Z form in the case where R and R' are both hydrogen atoms or equal alkyl groups, are preferred in that more useful liquid crystalline materials can be obtained.

The liquid crystal composition provided by the present invention is preferred to be a liquid crystal dielectric composition comprising a component (A) containing at least one of compounds expressed by the formula (I), and besides, a component (B) containing at least one of compounds of a high dielectric anisotropy of $\Delta\epsilon \geq 5$, a component (C) containing at least one of a low dielectric anisotropy of $|\Delta\epsilon| < 5$ and a component (D) containing at least one of compounds having a clear point exceeding 80° C., and if necessary, another component (E).

Preferable compounds for the component (B) are shown below.

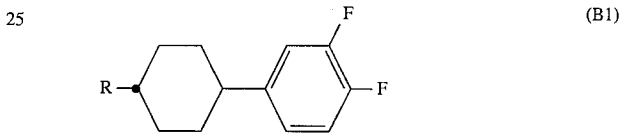
(B1)

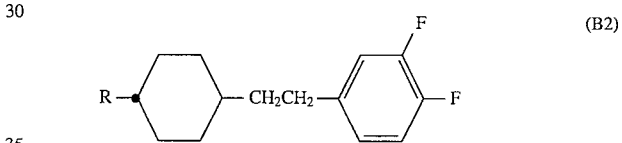
(B2)

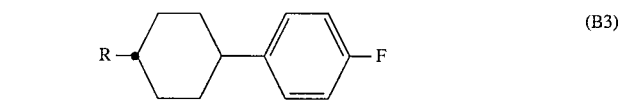
(B3)

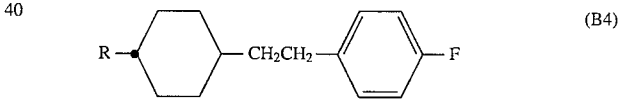
(B4)

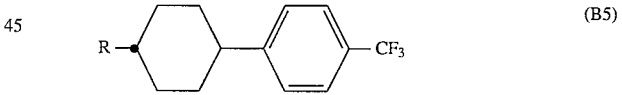
(B5)

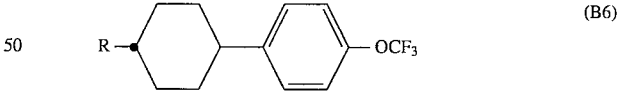
(B6)

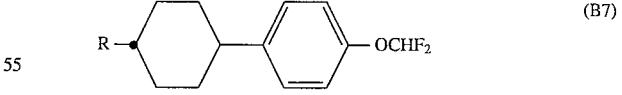
(B7)

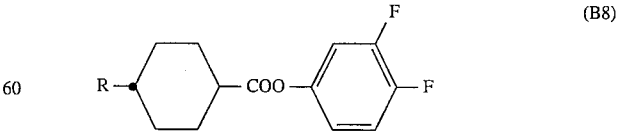
(B8)

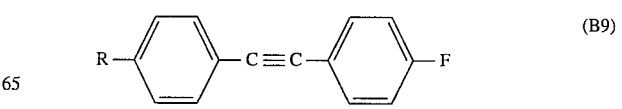
(B9)

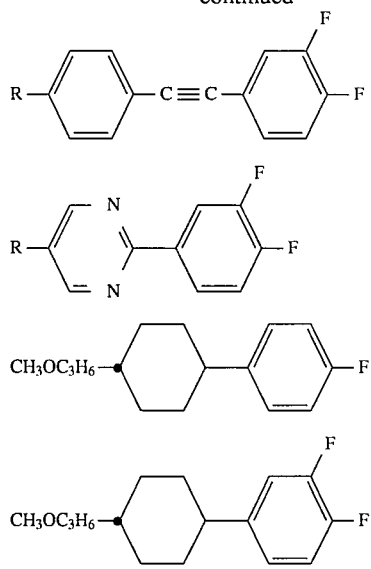

(B10)
(B11)
(B12)
(B13)

In the above compounds, R represents an alkyl group or an alkenyl group of 1 to 10 carbon atoms, and one carbon atom of the groups or two carbon atoms not adjacent to each other in the group may be replaced by oxygen atom(s).

Preferable compounds for the component (C) are shown below.

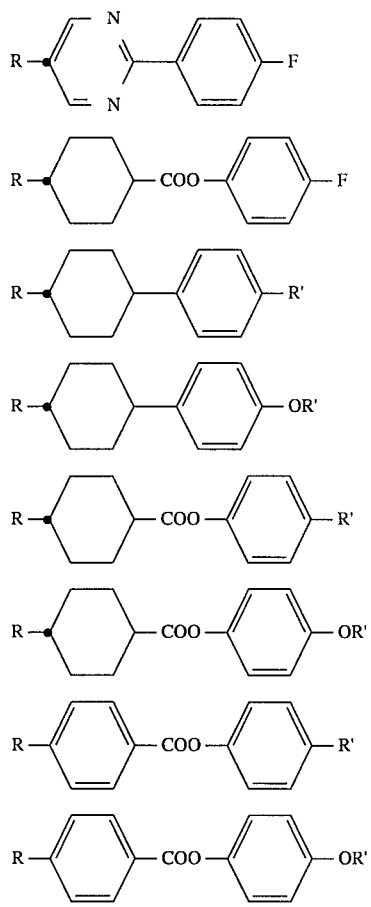

(C1)
(C2)
(C3)
(C4)
(C5)
(C6)
(C7)
(C8)

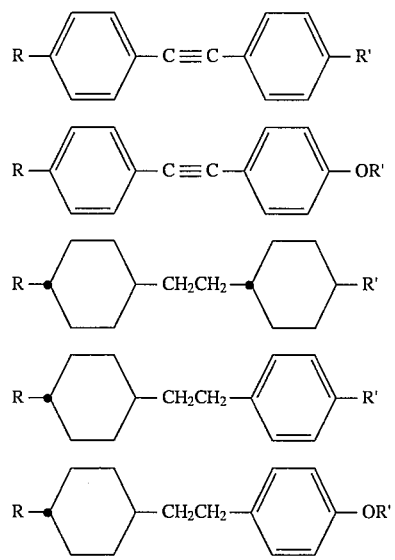

(C9)
(C10)
(C11)
(C12)
(C13)

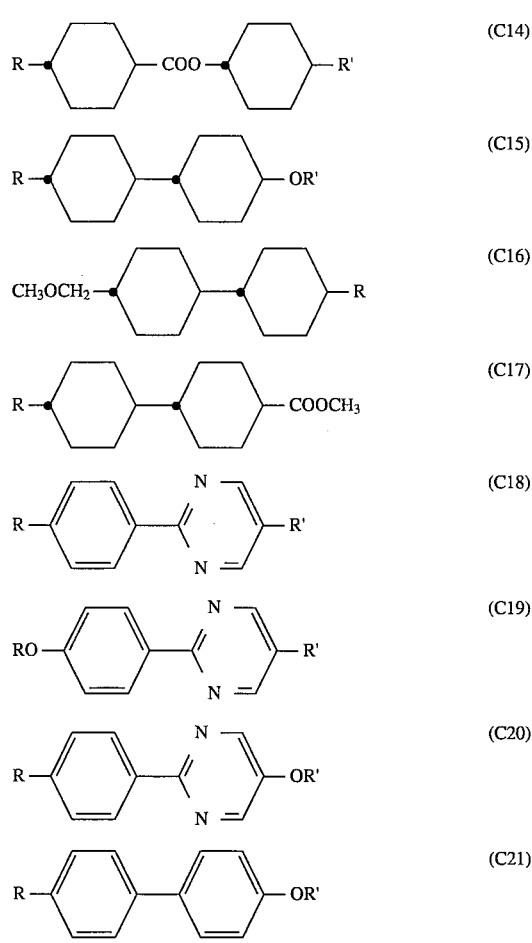

(C14)
(C15)
(C16)
(C17)
(C18)
(C19)
(C20)
(C21)

In these compounds, R and R' represent an alkyl group or alkenyl group of 1 to 10 carbon atoms, and one carbon atom of the groups or two carbon atoms not adjacent to one another in the group may be replaced by oxygen atom(s).

Preferable compounds for the component (D) are shown below.
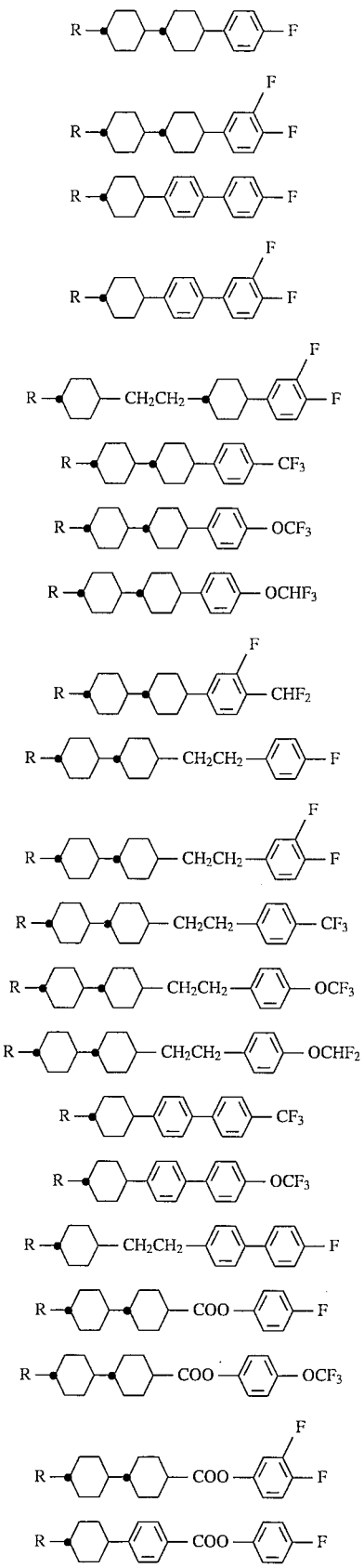
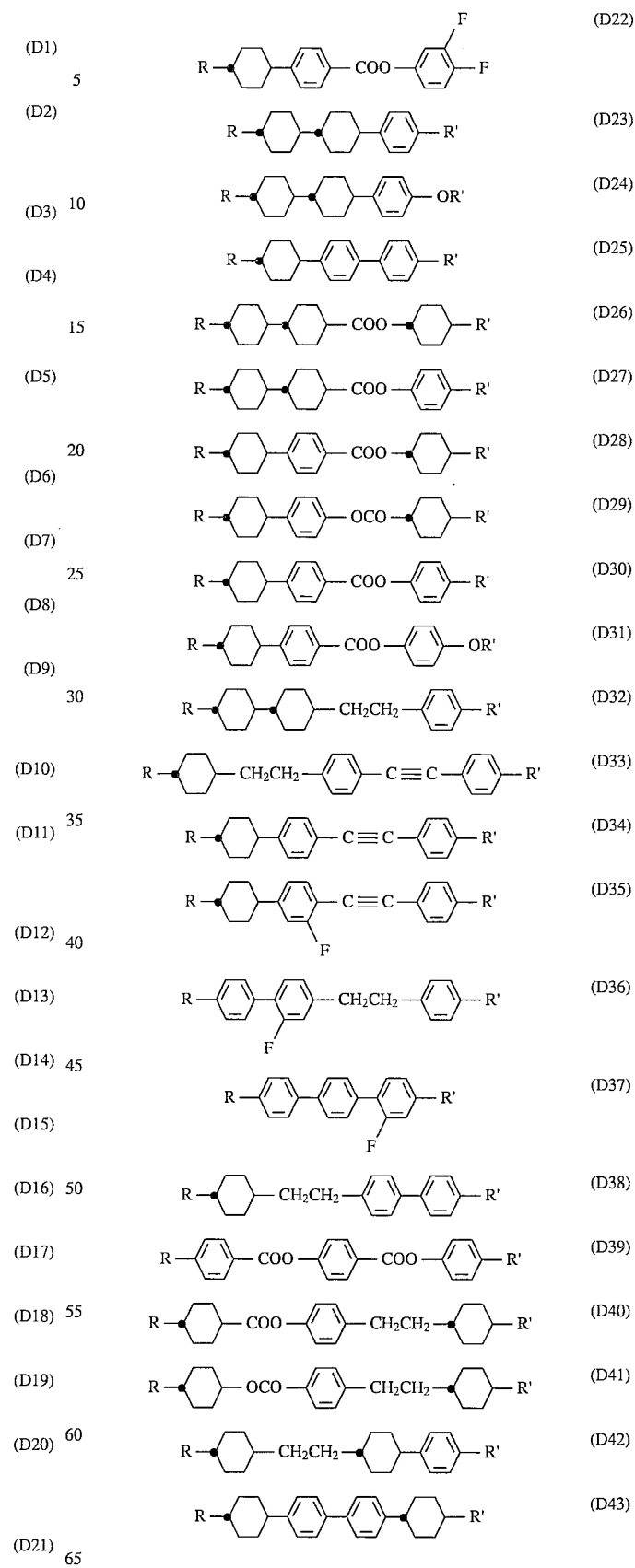

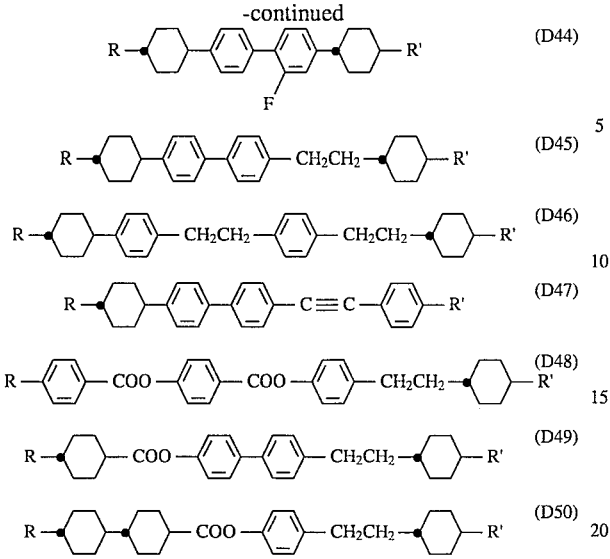

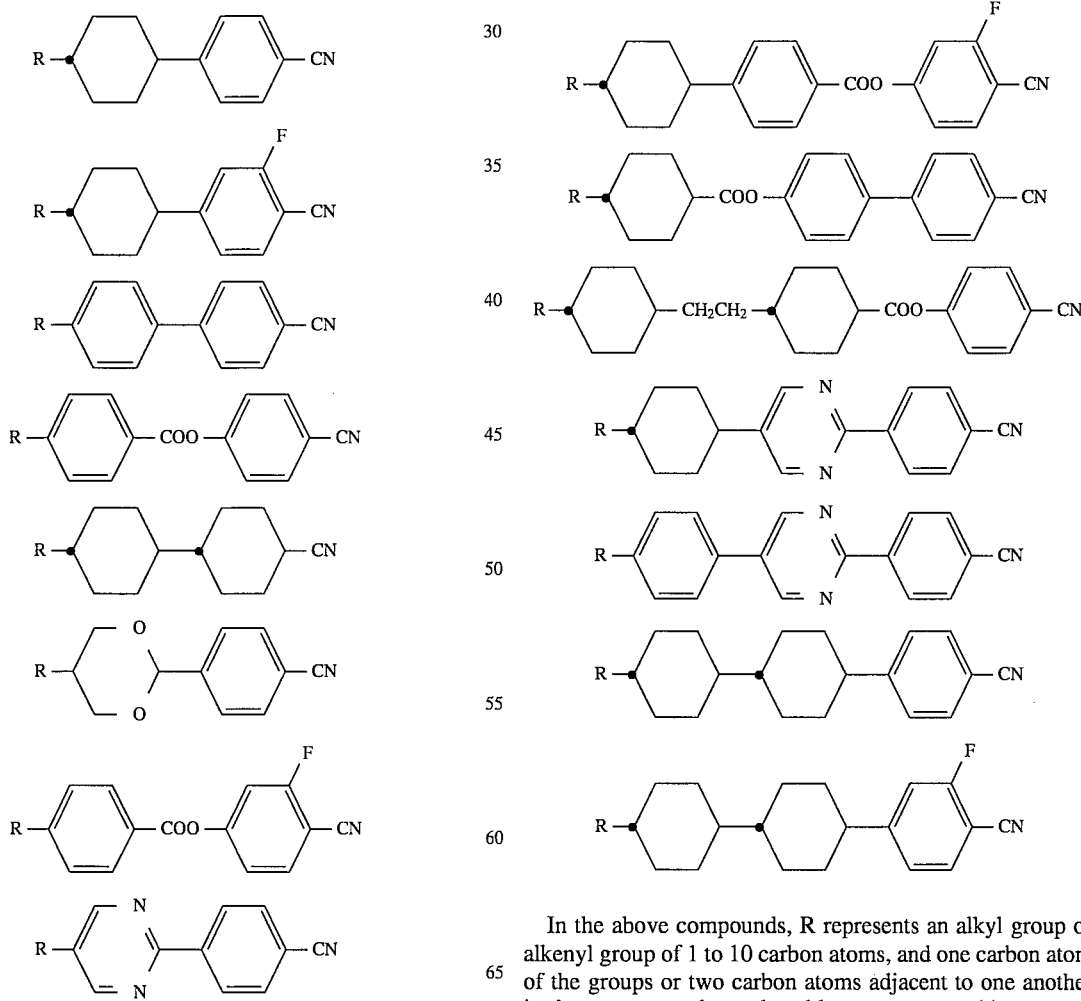

In the above compounds, R and R' represent an alkyl group or alkenyl group of 1 to 10 carbon atoms, and one carbon atom of the group or two carbon atoms not adjacent to one another in the group may be replaced by oxygen atom.

Preferable compounds for the component (E) are shown below.

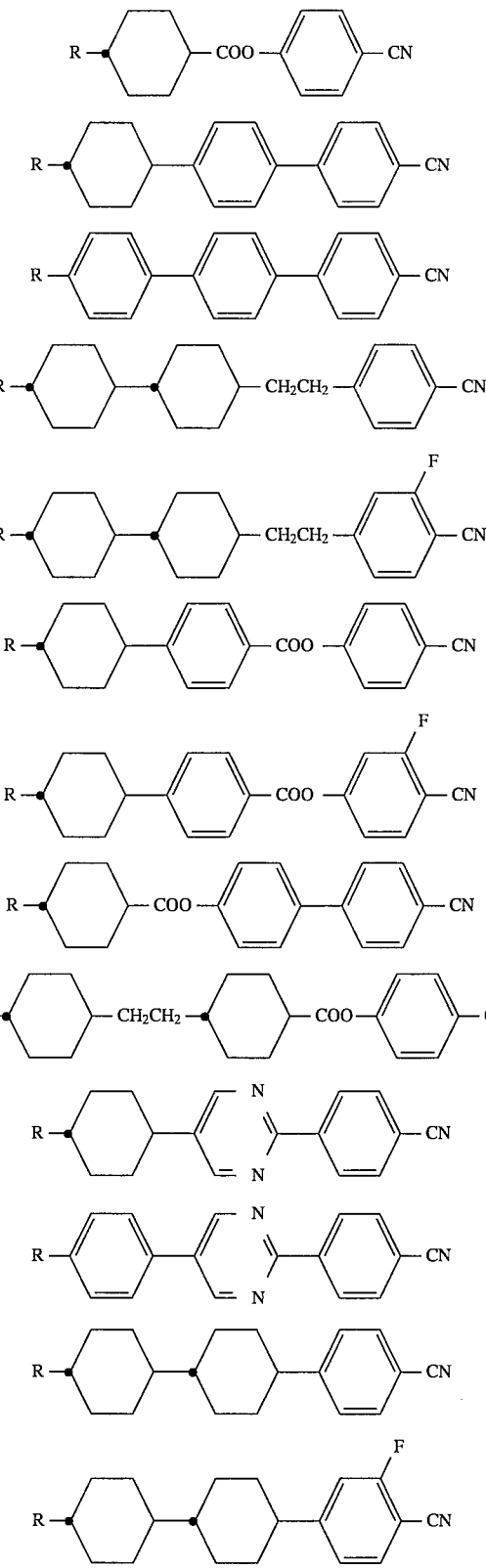

In the above compounds, R represents an alkyl group or alkenyl group of 1 to 10 carbon atoms, and one carbon atom of the groups or two carbon atoms adjacent to one another in the group may be replaced by oxygen atom(s).

The composition according to the present invention contains at least one compound expressed by the formula (I) preferably in a proportion of 0.1 to 40% by weight in order to obtain superior liquid crystalline characteristics. (Production process)

The compound of the present invention can be produced from an aldehyde derivative expressed by the formula (II)

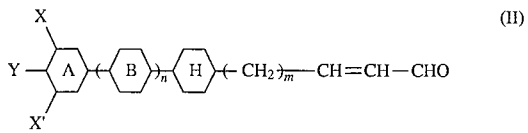
(II)

wherein A and B each independently represent 1,4-cyclohexylene or 1,4-phenylene; n represents 0 or 1; m represents an integer of 0 to 2; X and X' each independently represent a hydrogen atom or a fluorine atom when A represents 1,4-phenylene, or a hydrogen atom when A represents 1,4-cyclohexylene; and Y represents an alkyl group; a halogen atom, a cyano group an alkoxy group, a methyl group substituted by 1 to 3 halogen atoms or a trihaloalkoxy group when A represents 1,4-phenylene, or an alkyl group, an alkoxy group, a methyl group substituted by 1 to 3 halogen atoms or a trihaloalkoxy group when A represents 1,4-cyclohexylene, and an olefinizing reagent. Namely, the compound of the present invention can be obtained by subjecting the compound (II) and a phosphorus ylide compound expressed by the formula (III)

wherein R and R' are as defined above, to Wittig reaction, or by reacting an aldehyde derivative expressed by the formula (II) with an alkane diiodide expressed by the formula (IV)

wherein R and R' are as defined above, in the presence of chromium chloride (II).

The reaction of the compound of the formula (II) with the compound of the formula (III) can be carried out according to a generally known method as disclosed in Organic Reaction, Vol. 14, 270, 1965. Namely, a phosphonium salt expressed by the formula (V)

wherein Z represents a halogen atom and R and R' are as defined above, is treated with a base to generate phosphorus ylide expressed by the formula (III), followed by adding an aldehyde without isolating phosphorus ylide to obtain the compound of the present invention. It is preferred to carry out this reaction in a suitable solvent. The solvent may be sufficient unless it inhibits the reaction. Hydrocarbon solvents such as hexane, heptane, xylene, benzene, toluene, etc., ether solvents such as tetrahydrofuran, diethyl ether, t-butyl methyl ether, dioxane, etc., and in cases, N,N-dimethylformamide, hexamethylphosphoric triamide, dimethylsulfoxide, etc. are suitable. They are usable as a single solvent or a mixed solvent.

It is indispensable for this reaction to use a base, and as the base used, potassium t-butoxide, sodium methoxide, sodium hydride, sodium dimsyl, n-butyllithium, lithium diisopropylamide, pyridine, triethylamine, etc. are usable, but among these, potassium t-butoxide, sodium methoxide, sodium hydride, sodium dimsyl, and n-butyllithium are preferable, since the generated phosphorine ylide compound (III) is stable at a room temperature and good in the yield. Further, in particular potassium t-butoxide is preferable since it is easily prepared and dealt with. The reaction temperature in this case can be usually chosen within a range of −78° C. to the boiling point of the solvent, but a range of −78° C. to a room temperature is preferable since the formed phosphorus ylide can be reacted stably and sufficiently. Further, after the completion of the reaction, usually by-produced phosphin oxide is removed to the outside by filtration, followed by removing the solvent, whereby it is possible to obtain a raw product of the compound of the present invention. The resulting raw product can be purified according to a conventional method, that is, by distillation, recrystallization or column chromatography or by a combination thereof.

The reaction of the aldehyde derivative of the formula (II) with the diiodide of the formula (IV) can be carried out according to a generally known method, as disclosed in J. Am. Chem. Soc., Vol. 109, No. 3, 1987. Namely, a reagent is generated from an alkanediiodide and chromium chloride (II) in situ, followed by adding an aldehyde derivative of the formula (II), to obtain the compound of the present invention. This reaction is preferred to be carried out in the presence of a solvent. As the solvent used, those which do not inhibit the reaction may be sufficient. An aprotic polar solvent such as N,N-dimethylformamide, dioxane, tetrahydrofuran, etc. is preferred in that the yield is good. This reaction can be also carried out in the presence of a base. As the base used, it can be chosen from among various amine derivatives, but ethylenediamine, tetramethylethylenediamine, etc. are more preferred. The chromium chloride (II) used in the reaction is equivalent preferred to use in a quantity of twice or more the mol of the alkane diiodide, but it is more preferred to use in a quantity of three times or more the mol equivalent thereof, in order to obtain a sufficient yield. The reaction temperature can be chosen usually within a range of −78° C. to the boiling point of the solvent, but a range of 0° C. to the boiling point of the solvent is preferred since the formed reagent can be reacted stably and sufficiently. The thus formed compound of the present invention is extracted from the reaction system with a suitable solvent, followed by purification processing such as distillation, recrystallization or column chromatography or a combination thereof, to obtain the compound in a purified form.

Further, the compound of the present invention of the formula (I) wherein m=1 can be obtained in a pure form, by separating only a desirable isomer from the mixture of isomers relative to the position of the alkyl chain containing dienyl group at the terminal of the molecule, prepared according to the above process, by a purification process such as a silica gel column chromatography, for example, or by separating the isomer by means of a clathrate treatment using a host compound such as urea or the like, but it can be more efficiently produced according to a process as shown below. Namely, an ester derivative expressed by the formula (VI)

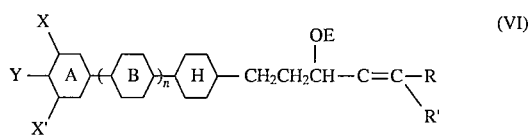
(VI)

wherein R and R' each independently represent a hydrogen atom or an alkyl group of 1 to 5 carbon atoms; A and B each independently represent 1,4-cyclohexylene or 1,4-phenylene; n represents 0 or 1; X and X' each independently represent a hydrogen atom or a fluorine atom when A is 1,4-phenylene, or a hydrogen atom when A is 1,4-cyclohexylene; Y represents an alkyl group, a halogen atom, a cyano group, an alkoxy group, a methyl group substituted by 1 to 3 halogen atoms or a trihaloalkoxy group when A is 1,4-phenylene, and an alkyl group, an alkoxy group, a methyl group substituted by 1 to 3 halogen atoms or a trihaloalkoxy group when A is 1,4-cyclohexylene; E represents an acetyl group, a toluenesulfonyl group, a methanesulfonyl group or a trifluoromethanesulfonyl group; and R and R' are not simultaneously an alkyl chain of 4 or more carbon atoms, is treated with a base, or a divalent palladium salt is reacted with the above ester derivative in the presence of triphenylphosphine.

Production conditions in the present process are described in details below. Examples of the base used when the compound of the present invention is obtained by treating the ester derivative expressed by the formula (VI) in the presence of a base, are as follows: alkali metal salts such as potassium carbonate, sodium carbonate, sodium hydrogen carbonate, potassium acetate, etc., organic amine such as triethylamine, diethylamine, dimethylaminopyridine, 2,6-lutidine, pyridine, morphorine, DBU, etc., metal alkoxides such as sodium methoxide, potassium methoxide, potassium t-butoxide, etc., organic metals such as methyllithium, phenyllithium, butyllithium, etc., metal hydrides such as sodium hydride, calcium hydride, etc., and metal amides such as sodium amide, etc., but among these, it is preferred to use metal alkoxides or metal hydrides since the reaction proceeds rapidly and side reaction is few. Further, this reaction is preferred to be carried out in a solvent. Examples of the solvent used are ether solvents such as tetrahydrofuran, dioxane, ethylene glycol dimethyl ether, etc., hydrocarbon solvents such as benzene, toluene, xylene, etc., alcohol solvents such as methanol, ethanol, butanol, etc., and aprotic, polar solvents such as acetone, dimethylsulfoxide, N,N-dimethylformamide, etc., but tetrahydrofuran, dioxane, butanol, dimethylsulfoxide, etc. are preferable in that the reaction proceeds rapidly and the processability is good. The reaction temperature can be chosen within a range of −78° C. to the boiling point of the solvent, but a range of 0° C. to 100° C. is preferred in that the reaction proceeds rapidly and side reactions are few. Further, in the reaction of reacting the ester derivative expressed by the formula (VI) in the presence of a palladium catalyst to obtain the compound of the present invention, a ligand is necessary besides a divalent palladium salt. Examples of the divalent palladium salts used in this case are palladium acetate, palladium chloride, dichlorobis(acetonitrile)palladium, etc. Examples of the ligand are triphenylphosphine, trialkylphosphine, 1,2-bis-(diphenylphosphino)ethane, etc. Further, the reaction proceeds rapidly in the presence of a base. Examples of the base are calcium carbonate, sodium hydrogen carbonate, potassium acetate, sodium hydroxide, potassium hydroxide, sodium hydride, triethylamine, pyridine, etc. Examples of the solvent used are 1,4-dioxane, tetrahydrofuran, ethylene glycol dimethyl ether, dimethylsulfoxide, N,N-dimethylformamide, pyridine etc., but tetrahydrofuran, dioxane, etc. are more preferable in that the boiling points thereof are suitable. This reaction can be carried out within a range of −78° C. to the boiling point of the solvent, but a range of a room temperature to 150° C. is preferred in that the reaction itself proceeds rapidly.

The aldehyde derivative of the formula (II) as a preparation intermediate of the compound of the present invention can be obtained according to a process shown below, for example:

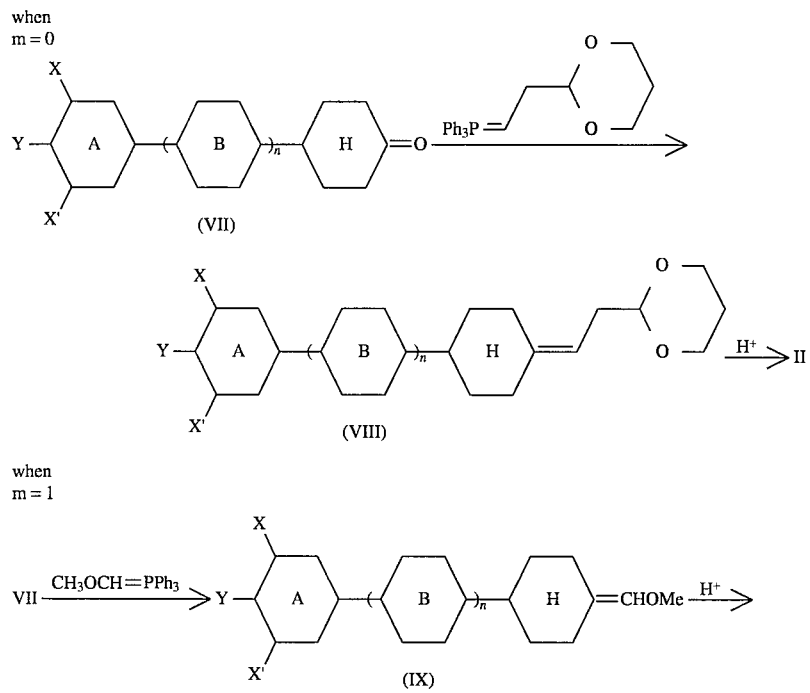

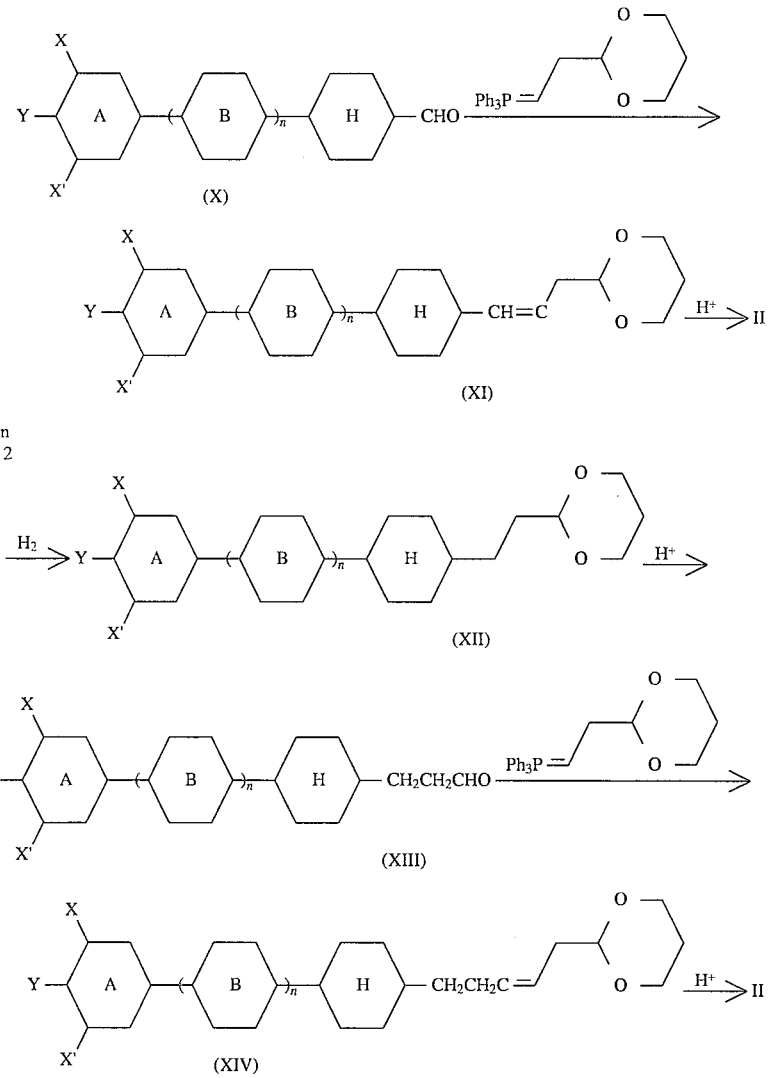

when
m = 2

In the above equations, A and B each independently represent 1,4-cyclohexylene or 1,4-phenylene; n represents 0 or 1; m represents an integer of 0 to 2; X and X' each independently represent a hydrogen atom or a fluorine atom when A is 1,4-phenylene, or a hydrogen atom when A is 1,4-cyclohexylene; Y represents an alkyl group, a halogen atom, a cyano group, an alkoxy group, a methyl group substituted by 1 to 3 halogen atoms or a trihaloalkoxy group when A is 1,4-phenylene, or an alkyl group, an alkoxy group, a methyl group substituted by 1 to 3 halogen atoms or a trihaloalkoxy group when A is 1,4-cyclohexylene.

Namely, the aldehyde derivative expressed by the formula (II), in the case of m=0, can be obtained by reacting a cyclohexanone derivative of the formula (VII) with a phosphorus ylide which is prepared from (1,3-dioxan-2-yl)ethyltriphenylphosphonium bromide which is shown in the reaction equation and easily commercially available, to obtain a 1,3-dioxane derivative of the formula (VIII), and treating this derivative with an acid.

Further, in the case of m=1, the compound (II) is prepared as follows. The cyclohexanone derivative of the formula (VII) is treated with a phosphorus ylide which is prepared from methoxymethyltriphenylphosphonium chloride shown in the reaction equation and easily commercially available, to obtain a methyl vinyl ether of the formula (IX), followed by treating this ether with an acid to obtain an acetaldehyde derivative of the formula (X). The aldehyde derivative (II) is obtained by treating this acetaldehyde (X) with a phosphorus ylide prepared from (1,3-dioxan-2-yl)ethyltriphenylphosphonium bromide to obtain a 1,3-dioxane derivative, and treating this derivative with an acid.

Further, in the case of m=2, the compound (II) is prepared as follows. The 1,3-dioxane derivative of the formula (VIII) is hydrogenated in the presence of a catalyst to obtain a dioxane derivative of the formula (XII), followed by treating this derivative with an acid to obtain a propionaldehyde derivative of the formula (XIII), reacting this derivative with a phosphorus ylide which is prepared from (1,3-dioxan-2-yl)ethyltriphenylphosphonium bromide to obtain a 1,3-dioxane derivative of the formula (XIV), treating this derivative with an acid to obtain an aldehyde derivative of the formula (II).

Further, an ester derivative of the formula (VI) as an intermediate in the preparation of the compound of the present invention in the case of m=1 can be prepared as follows, for example.

VIII $\xrightarrow{\text{ZMgCH=CRR'}}$

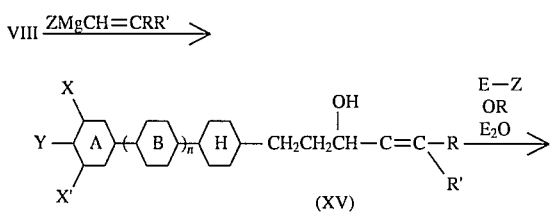

(XV) $\xrightarrow[E_2O]{\begin{array}{c}E-Z\\ OR\end{array}}$ VI

In the equations, A and B each independently represent 1,4-cyclohexylene or 1,4-phenylene; n represents 0 or 1; m represents an integer of 0 to 2; X and X' each independently represent a hydrogen atom or a fluorine atom when A is 1,4-phenylene, or a hydrogen atom when A is cyclohexylene; Y represents an alkyl group, a halogen atom, a cyano group, an alkoxy group, a methyl group substituted by 1 to 3 halogen atoms or a trihaloalkoxy group when A is 1,4-phenylene or an alkyl group, an alkoxy group, a methyl group substituted by 1 to 3 halogen atoms or a trihaloalkoxy group when A is 1,4-cyclohexylene; E represents an acetyl group, a toluenesulfonyl group, a methanesulfonyl group or a trifluoromethanesulfonyl group; and Z represents a halogen atom.

Namely, a substituted vinyl-Grignard reagent is addition-reacted to an aldehyde derivative of the formula (XIII), followed by reacting an acid halide or an acid anhydride with the resulting allyl alcohol derivative.

The present invention will be described in more detail by way of examples, but it should not be construed to be limited thereto.

In the following examples, the temperature properties of the mesophases are indicated by symbols N (nematic), I (istropic), S (smectic) and $C_P$= clearing point. $\Delta\epsilon$ represents dielectric anisotropy calculated by the equation of $\Delta\epsilon=\epsilon_{\parallel}-\epsilon_{\perp}$. $K_{33}/K_{11}$ represents the ratio of the elastic constants of bending and expansion. $\Delta n$ represents an optical anisotropy. $\eta_{20}$ represents a viscosity at 20° C. $V_{th}$ represents a threshold voltage.

EXAMPLE 1

Preparation of 1-(4-(4-cyanophenyl)cyclohexyl)-1E, 3-butadiene

Into a three-necked flask equipped with a dropping funnel, a three-way cock and a thermometer, was placed 2-(1,3-dioxan-2-yl)ethyltriphenylphosphonium bromide (12.2 g, 27 mmols), followed by adding tetrahydrofuran (200 ml), suspending, stirring the suspension under ice cooling till the liquid temperature reached 10° C., adding to the reaction mixture, potassium t-butoxide (30 g, 27 mmols), elevating the temperature up to room temperature under ice cooling for one hour, stirring the mixture for one hour, dropwise adding a tetrahydrofuran (50 ml) solution of 4-(4-cyanophenyl)cyclohexanone (5.0 g, 25 mmols) from the dropping funnel over 30 minutes. The reaction mixture was stirred for 5 hours after completion of the dropwise addition, followed by adding ether (100 ml), allowing the mixture to stand, filtering off deposited insoluble substance, concentrating the filtrate under reduced pressure, and isolating and purifying the resulting pale brown oil by means of silica gel column chromatography, to obtain 1-(2-(1,3-dioxan-2-yl)ethylidene)-4-(4-cyanophenyl)cyclohexane (4.1 g, 14 mmols).

The thus obtained cyclohexane derivative was dissolved in a mixed solvent of acetone (100 ml) and 2N hydrochloric acid (10 ml), followed by heating the solution under reflux for 4 hours, cooling the reaction solution down to room temperature after completion of the stirring, adding water, extracting with ether (200 ml), drying the resulting organic layer over anhydrous magnesium sulfate, and concentrating under reduced pressure to obtain 3-(4-(4-cyanophenyl)cyclohexyl)-2E-propenal (2.9 g, 12 mmols). This product was used in the subsequent reaction without any purification.

Methyltriphenylphosphonium bromide (5.3 g, 15 mmols) was dissolved in tetrahydrofuran (50 ml), followed by adding potassium t-butoxide (1.6 g, 14 mmols) under ice cooling with stirring, elevating the temperature up to room temperature under ice cooling for one hour, stirring for one hour, dropwise adding a tetrahydrofuran (20 ml) solution of the above-obtained 3-(4-(4-cyanophenyl)cyclohexyl)-2E-propenal to the above solution, further stirring the reaction solution for 5 hours after completion of the dropwise addition, adding ether, allowing it to stand for one hour, filtering off deposited insoluble substance, concentrating the filtrate under a reduced pressure, isolating and purifying the resulting pale brown oil by means of silica gel column chromatography, and recrystallizing from ethanol, to obtain the captioned compound (1.0 g, 4.2 mmols). Its phase transition temperature is shown below.

C—N 94.5 N—I 117.0° C.

In the same manner as the above, the following compounds are prepared:

1-(4-(4-ethylphenyl)cyclohexyl)-1E,3-butadiene 1-(4-(4-propylphenyl)cyclohexyl)-1E,3-butadiene 1-(4-(4-pentylphenyl)cyclohexyl)-1E,3-butadiene 1-(4-(3-fluoro-4-cyanophenyl)cyclohexyl)-1E,3-butadiene 1-(4-(3,5-difluoro-4-cyanophenyl)cyclohexyl)-E,3-butadiene

EXAMPLE 2

Preparation of 1-(4-(3,4,5-trifluorophenyl)cyclohexyl)-1E,3-butadiene

Into a three-necked flask equipped with a dropping funnel, a three-way cock and a thermometer was placed 2-(1,3-dioxan-2-yl)ethyltriphenylphosphonium bromide (12.2 g, 27 mmols), followed by adding tetrahydrofuran (200 ml), suspending it, stirring under ice cooling till the liquid temperature reached 10° C., adding potassium t-butoxide (3.0 g, 27 mmols) to the reaction mixture, further elevating the temperature up to room temperature under ice cooling for one hour, stirring for one hour, dropwise adding a tetrahydrofuran (50 ml) solution of 4-(3,4,5-trifluorophenyl) cyclohexanone (5.7 g, 25 mmols) from the dropping funnel over 30 minutes, further stirring the reaction mixture for 5 hours after completion of the dropwise addition, adding ether (100 ml), allowing to stand for one hour, filtering off deposited insoluble substance, concentrating the filtrate under reduced pressure and isolating and purifying the resulting pale brown oil by means of silica gel column chromatography, to obtain 1-(2-(1,3-dioxan-2-yl)ethylidene)-4-(3,4,5-trifluorophenyl)cyclohexane.

The thus obtained cyclohexane derivative (4.5 g, 14 mmols) was dissolved in a mixed solvent of acetone (100 ml) with 2N hydrochloric acid (10 ml), followed by heating the solution under reflux for 4 hours, cooling the reaction mixture down to room temperature after completion of the stirring, adding water, extracting with ether (200 ml), drying the resulting organic layer over anhydrous magnesium sulfate and concentrating under reduced pressure, to obtain 3-(4-(3,4,5-trifluorophenyl)cyclohexyl)-2E-propenal. This product was used in the subsequent reaction without any purification.

Methyltriphenylphosphonium bromide (5.3 g, 15 mmols) was dissolved in tetrahydrofuran, followed by adding potassium t-butoxide (1.6 g, 14 mmols) under ice cooling with stirring, further elevating the temperature up to room temperature under ice cooling, stirring for one hour, and dropwise adding to the reaction mixture, a tetrahydrofuran (20 ml) solution of the aboveobtained 3-(4-(3,4,5-trifluorophenyl)cyclohexyl)-2E-propenal (3.0 g, 12 mmols). The reaction mixture was stirred for 5 hours after completion of the dropwise addition, adding ether, allowing the mixture to stand for one hour, filtering off deposited insoluble substance, concentrating the filtrate under reduced pressure, isolating and purifying the resulting pale brown oil by means of silica gel column chromatography, and recrystallizing from ethanol, to obtain the captioned compound.

In the same process as the above, the following compounds are prepared:

1-(4-(4-fluorophenyl)cyclohexyl)-1E,3-butadiene (C—I: 42.5° C.)

1-(4-(3,4-difluorophenyl)cyclohexyl)-1E,3-butadiene

EXAMPLE 3

Preparation of 1-(4-(4-trifluoromethylphenyl)cyclohexyl)-1E,3-butadiene

Into a three-necked flask equipped with a dropping funnel, a three-way cock and a thermometer was placed 2-(1,3-dioxan-2-yl)ethyltriphenylphosphonium bromide (12.2 g, 27 mmols), followed by adding tetrahydrofuran (100 ml), suspending, and stirring under ice cooling till the liquid temperature reached 10° C. The resulting reaction mixture was added potassium t-butoxide (3.0 g, 27 mmols), followed by elevating the temperature up to room temperature under ice cooling, stirring for one hour, dropwise adding a tetrahydrofuran (50 ml) solution of 4-(4-trifluoromethylphenyl)cyclohexanone (6.0 g, 25 mmols) over 30 minutes from the dropping funnel, further stirring the reaction mixture for 5 hours after completion of the dropwise addition, adding ether (100 ml), allowing to stand for one hour, filtering off deposited insoluble substance, concentrating the filtrate under reduced pressure and isolating and purifying the resulting pale brown oil by means of silica gel column chromatography, to obtain 1-(2-(1,3-dioxan-2-yl)-ethylidene)-4-(4-trifluoromethylphenyl)cyclohexane.

The thus obtained cyclohexane derivative (4.7 g, 14 mmols) was dissolved in a mixed solvent of acetone (100 ml) with 2N hydrochloric acid (10 ml), followed by heating the solution under reflux for 4 hours. The resulting reaction mixture was cooled down to room temperature after completion of the stirring, followed by adding water, extracting with ether (150 ml), drying the resulting organic layer over anhydrous magnesium sulfate and concentrating under reduced pressure to obtain 3-(4-(4-trifluoromethylphenyl)cyclohexyl)-2E-propenal. This product was used in the subsequent reaction without purification.

Methyltriphenylphosphonium bromide (5.3 g, 15 mmols) was dissolved in tetrahydrofuran (50 ml), followed by adding potassium t-butoxide (1.6 g, 14 mmols) while stirring the solution under ice cooling, further elevating the temperature up to room temperature under ice cooling for one hour, stirring for one hour, dropwise adding to the reaction mixture tetrahydrofuran (30 ml) solution of the above-obtained 3-(4-(4-trifluoromethylphenyl)cyclohexyl)-2E-propenal (3.4 g, 12 mmols), further stirring the reaction mixture for 5 hours after completion of the dropwise addition, adding ether (100 ml), allowing the mixture to stand for one hour, filtering off deposited insoluble substance, concentrating the filtrate under reduced pressure, isolating and purifying the resulting pale brown oil by means of silica gel column chromatography and recrystallizing from ethanol, to obtain the captioned compound.

In the same manner as the above, the following compounds are prepared:

1-(4-(3-fluoro-4-trifluoromethylphenyl)cyclohexyl)-1E,3-butadiene 1-(4-(3,5-difluoro-4-trifluoromethylphenyl)cyclohexyl)-1E,3-butadiene

EXAMPLE 4

Preparation of 1-(4-(3-fluoro-4-trifluoromethoxyphenyl)cyclohexyl)-1E,3-butadiene Into a three-necked flask equipped with a dropping funnel, a three-way cock and a thermometer was placed 2-(1,3-dioxan-2-yl)ethyltriphenylphosphonium bromide (9.1 g, 20 mmols), followed by adding tetrahydrofuran (100 ml), suspending, stirring under ice cooling till the liquid temperature reached 10° C. The resulting reaction mixture was added potassium t-butoxide (2.2 g, 20 mmols) followed by elevating the temperature up to room temperature under ice cooling for one hour, stirring for one hour, dropwise adding a tetrahydrofuran (50 ml) solution of 4-(3-fluoro-4-trifluoromethoxyphenyl)cyclohexanone (5.5 g, 20 mmols) over 30 minutes from the dropping funnel, further stirring the reaction mixture for 5 hours after completion of the dropwise addition, adding ether (100 ml), allowing to stand for one hour, filtering off deposited insoluble substance, concentrating the filtrate under reduced pressure, and isolating and purifying the resulting pale brown oil by means of silica gel column chromatography, to obtain 1-(2-(1,3-dioxan-2-yl)ethylidene)-4-(3-fluoro-4-trifluoromethoxyphenyl)cyclohexane.

The thus obtained cyclohexane derivative (5.6 g, 15 mmols) was dissolved in a mixed solvent of acetone (100 ml) with 2N hydrochloric acid (10 ml), followed by heating the solution under reflux for 4 hours, cooling the reaction mixture down to room temperature after completion of the stirring, adding water, extracting with ether (100 ml), drying the resulting organic layer over anhydrous magnesium sulfate, and concentrating under reduced pressure, to obtain 3-(4-(3-fluoro-4-trifluoromethoxyphenyl)cyclohexyl)-2E-propenal. This product was used in the subsequent reaction without any purification.

Methyltriphenylphosphonium bromide (6.0 g, 17 mmols) was dissolved in tetrahydrofuran (60 ml), followed by adding potassium t-butoxide (1.9 g, 17 mmols) while stirring the solution under ice cooling with stirring, further elevating the temperature up to room temperature under ice cooling for one hour, stirring for one hour, dropwise adding to the reaction mixture, a tetrahydrofuran (30 ml) solution of the above-obtained 3-(4-(3-fluoro-4-trifluoromethoxyphenyl)cyclohexyl)-2E-propenal (4.7 g, 15 mmols), further stirring the reaction mixture for 5 hours after completion of the dropwise addition, adding ether (100 ml), allowing to stand for one hour, filtering off deposited insoluble substance, concentrating the filtrate under reduced pressure, isolating and purifying the resulting pale brown oil by means of silica gel column chromatography and recrystallizing from ethanol, to obtain a pure, captioned compound.

In the same manner as the above, the following compounds are prepared:

1-(4-(4-trifluoromethoxyphenyl)cyclohexyl)-1E,3-butadiene 1-(4-(3-fluoro-4-trifluoromethoxyphenyl)cyclohexyl)-1E,3-butadiene 1-(4-(3,5-difluoro-4-trifluoromethoxyphenyl)cyclohexyl)-1E,3-butadiene

EXAMPLE 5

Preparation of 1-(4-(4-(3,4-difluorophenyl)cyclohexyl)cyclohexyl)-1E,3-butadiene Into a three-necked flask equipped with a dropping funnel, a three-way cock and a thermometer was placed 2-(1,3-dioxan-2-yl)ethyltriphenylphosphonium bromide (12.3 g, 27 mmols), followed by adding tetrahydrofuran (100 ml), suspending, and stirring under ice cooling till the liquid temperature reached 10° C. The reaction mixture was added potassium t-butoxide (3.0 g, 27 mmols), followed by elevating the temperature up to room temperature under ice cooling for one hour, stirring for one hour, and dropwise adding a tetrahydrofuran (50 ml) solution of (4-(3,4-difluorophenyl)cyclohexylcyclohexanone (7.3 g, 25 mmols) over 30 minutes from the dropping funnel. Further, the resulting reaction mixture was stirred for 5 hours after completion of the dropwise addition, followed by adding ether (100 ml), allowing to stand for one hour, filtering off deposited insoluble substance, concentrating the filtrate under reduced pressure and isolating and purifying the resulting pale brown oil by means of silica gel column chromatography, to obtain 1-(2-(1,3-dioxan-2-yl)ethylidene)-4-(4-(3,4-difluorophenyl)cyclohexyl)cyclohexane.

The thus obtained cyclohexane derivative (6.6 g, 17 mmols) was dissolved in a mixed solvent of acetone (100 ml) with 2N hydrochloric acid (10 ml), followed by heating the solution under reflux for 4 hours, cooling the reaction mixture down to room temperature after completion of the stirring, adding water, extracting with ether (150 ml), drying the resulting organic layer over anhydrous magnesium sulfate, and concentrating under reduced pressure, to obtain 3-(4-(4-(3,4-difluorophenyl)cyclohexyl)cyclohexyl)2E-propenal. This product was used in the subsequent reaction without any purification.

Methyltriphenylphosphonium bromide (6.4 g, 18 mmols) was dissolved in tetrahydrofuran (50 ml), followed by adding potassium t-butoxide (2.0 g, 18 , mmols) while stirring the solution under ice cooling, further elevating the temperature up to room temperature under ice cooling for one hour, stirring for one hour, dropwise adding a tetrahydrofuran (50 ml) solution of the above-obtained 3-(4-(4-(3,4-difluorophenyl)cyclohexyl)cyclohexyl)-2E-propenal (5.3 g, 16 mmols) to the reaction mixture, further stirring the reaction liquid for 5 hours after completion of the dropwise addition, adding ether (150 ml), allowing to stand for one hour, filtering off deposited insoluble substance, concentrating the filtrate under reduced pressure, isolating and purifying the resulting pale brown oil by means of silica gel column chromatography and further recrystallizing from ethanol-methanol, to obtain a pure, captioned compound.

In the same manner as the above, the following compounds are prepared:

1-(4-(4-(4-cyanophenyl)cyclohexyl)cyclohexyl)-1E,3-butadiene 1-(4-(4-(4-fluorophenyl)cyclohexyl)cyclohexyl)-1E,3-butadiene 1-(4-(4-(4-ethylphenyl)cyclohexyl)cyclohexyl)-1E,3-butadiene 1-(4-(4-(4-propylphenyl)cyclohexyl)cyclohexyl)-1E,3-butadiene 1-(4-(4-(4-pentylphenyl)cyclohexyl)cyclohexyl)-1E,3-butadiene 1-(4-(4-(3-fluoro-4-cyanophenyl)cyclohexyl)cyclohexyl)-1E, 3-butadiene 1-(4-(4-(4-trifluoromethoxyphenyl)cyclohexyl)-cyclohexyl)-1E,3-butadiene 1-(4-(4-(3-fluoro-4-trifluoromethylphenyl)cyclohexyl)cyclohexyl)-1E, 3-butadiene 1-(4-(4-(4-trifluoromethoxyphenyl)cyclohexyl)cyclohexyl)-1E, 3-butadiene 1-(4-(4-(3-fluoro-4-trifluoromethoxyphenyl)cyclohexyl)cyclohexyl)-1E, 3butadiene 1-(4-(4-(3,5-difluoro-4-trifluoromethoxyphenyl)-cyclohexyl)cyclohexyl)-1E,3-butadiene 1-(4-(4-(3,4,5-trifluorophenyl)cyclohexyl)cyclohexyl)-1E,3-butadiene

EXAMPLE 6 preparation of 1-(4-(4-(4-propylphenyl)phenyl)cyclohexyl)-2E, 4-pentadiene

Into a three-necked flask equipped with a dropping funnel, a three-way cock and a thermometer was placed 2-(1, 3-dioxan-2-yl)ethyltriphenylphosphonium bromide (22.9 g, 50 mmols), followed by adding tetrahydrofuran (100 ml), suspending, stirring the suspension under ice cooling till the liquid temperature reached 10° C. The resulting reaction mixture is added pottasium t-butoxide (5.6 g, 50 mmols), followed by elevating the temperature up to room temperature under ice cooling for one hour, stirring for one hour, dropwise adding a tetrahydrofuran (100 ml) solution of (4-(4-propylphenyl)phenyl)cyclohexanone (14.0 g, 48 mmols) over 30 minutes from the dropping funnel, further stirring the reaction liquid for 5 hours after completion of the dropwise addition, adding ether (200 ml), allowing to stand for one hour, filtering off deposited insoluble substance, concentrating the filtrate under reduced pressure and isolating and purifying the resulting pale brown oil by means of silica gel column chromatography, to obtain 1-(2-(1,3-dioxane-2-yl)ethylidene)-4-(4-(4-propylphenyl)-phenylcyclohexane.

The thus obtained cyclohexane derivative (11.7 g, 30 mmols) was dissolved in ethanol (200 ml), followed by adding Pd-C (5%) (2.0 g), stirring in a hydrogen atmosphere overnight, filtering off the catalyst from the reaction mixture after completion of the reaction and concentrating the filtrate under reduced pressure to obtain 1-(2-((1,3-dioxan)-2-yl)ethyl)-4-(4-(4-propylphenyl)phenyl)cyclohexane.

This cyclohexane derivative (11.8 g, 30 mmols) was dissolved in toluene (100 ml), followed by adding formic acid (5 ml), heating the mixture under reflux for 5 hours, washing the reaction mixture with water after completion of the stirring, drying over anhydrous magnesium sulfate, concentrating under reduced pressure and isolating the resulting yellow oil, to obtain 3-(4-(4-(4-propylphenyl)phenyl)cyclohexyl)propanal. This product is used in the subsequent reaction without any purification.

The thus obtained propanal derivative (9.7 g, 29 mmols) is dissolved in tetrahydrofuran (100 ml), followed by dropwise adding a tetrahydrofuran solution (1.0M, 29 ml) of vinylmagnesium bromide while stirring the solution under ice cooling, elevating the temperature of the reaction mixture up to room temperature after completion of the dropwise addition, dropwise adding a saturated ammonium chloride solution (100 ml), extracting with ethyl acetate (200 ml), drying over anhydrous magnesium chloride and concentrating under reduced pressure, to obtain pale yellow crystals of 5-(4-(4-4-propylphenyl)phenyl)cyclohexyl)-3-hydroxy-1-pentene.

The above pentene derivative (9.0 g, 25 mmols) and acetic anhydride (3.0 g, 30 mmols) are dissolved in ether (200 ml), followed by dropwise adding pyridine (5 ml), while stirring the solution under ice cooling, stirring the reaction liquid under ice cooling for one hour, elevating the temperature up to room temperature, stirring for 3 hours, pouring the reaction mixture into ice water after completion of the reaction extracting with toluene (150 ml), washing the organic layer with water, drying over anhydrous magnesium sulfate and concentrating under reduced pressure to obtain 5-(4-(4-(4-propylphenyl)phenyl)cyclohexyl)-3-acetyloxy-1-pentene pale yellow oil.

The thus obtained acetic acid ester (8.0 g, 20 mmols) is dissolved in dioxane (150 ml), followed by adding palladium acetate (45 mg, 0.2 mmol), calcium carbonate (1.0 g) and triphenylphosphine (0.5 g, 2 mmols), heating the mixture under reflux for 5 hours, pouring the reaction mixture into ice water after completion of the reaction, extracting with toluene (100 ml), drying the resulting organic layer over anhydrous magnesium sulfate and drying under reduced pressure to obtain a mixture of stereoisomers of the captioned compound. The mixture is dissolved in ethanol (80 ml), followed by adding thiourea (5 g), stirring at room temperature overnight, collecting deposited crystals after completion of the agitation, by filtration, dissolving the crystals in dilute hydrochloric acid (100 ml), extracting with toluene (100 ml), drying the organic layer over anhydrous magnesium sulfate and concentrating under reduced pressure, to obtain a raw product of the captioned compound. This product is recrystallized from a mixed solvent of ethanol-methanol to obtain a pure, captioned compound.

In the same manner as the above, the following compounds are prepared:

1-(4-(4-fluorophenyl)cyclohexyl)-2Z,4-pentadiene 1-(4-(4-cyanophenyl)cyclohexyl)-2Z,4-pentadiene 1-(4-(3-fluoro-4-cyanophenyl)cyclohexyl)-2Z,4-pentadiene 1-(4-(4-ethylphenyl)cyclohexyl)-2Z,4-pentadiene 1-(4-(3,4-difluorophenyl)cyclohexyl)-2Z,4-pentadiene 1-(4-(4-trifluoromethylphenyl)cyclohexyl)-2Z,4-pentadiene 1-(4-(3-fluoro-4-trifluoromethylphenyl)cyclohexyl)-2Z,4-pentadiene 1-(4-(3,5-difluoro-4-trifluoromethylphenyl)cyclohexyl)-2Z,4-pentadiene 1-(4-(4-trifluoromethoxyphenyl)cyclohexyl)-2Z,4 -pentadiene 1-(4-(3-fluoro-4-trifluoromethoxyphenyl)cyclohexyl)-2Z,4-pentadiene 1-(4-(3,5-difluoro-4-trifluoromethoxyphenyl)cyclohexyl)-2Z,4-pentadiene 1-(4-(4-(4-fluorophenyl)phenyl)cyclohexyl)-2Z,4-pentadiene 1-(4-(4-(4-cyanophenyl)phenyl)cyclohexyl)-2Z,4-pentadiene 1-(4-(4-(3-fluoro-4-cyanophenyl)phenyl)cyclohexyl)-2Z,4-pentadiene 1-(4-(4-(4-ethylphenyl)phenyl)cyclohexyl)-2Z,4-pentadiene 1-(4-(4-(4-pentylphenyl)phenyl)cyclohexyl)-2Z,4-pentadiene 1-(4-(4-(3,4-fluorophenyl)phenyl)cyclohexyl)-2Z,4-pentadiene 1-(4-(4-(4-trifluoromethylphenyl)phenyl)cyclohexyl)-2Z,4-pentadiene 1-(4-(4-(3-fluoro-4-trifluoromethylphenyl)phenyl) cyclohexyl)-2Z,4-pentadiene 1-(4-(4-(3,5-difluoro-4-trifluoromethylphenyl)phenyl) cyclohexyl)-2Z,4-pentadiene 1-(4-(4-(4-trifluoromethoxyphenyl)phenyl)cyclohexyl)-2Z,4-pentadiene 1-(4-(4-(3-fluoro-4-trifluoromethoxyphenyl)phenyl) cyclohexyl)-2Z,4-pentadiene 1-(4-(4-(3,5-difluoro-4-trifluoromethoxyphenyl)phenyl) cyclohexyl)-2Z,4-pentadiene 1-(4-(4-(4-cyanophenyl)cyclohexyl)cyclohexyl)-2Z,4-pentadiene 1-(4-(4-(3,5-difluoro-4-trifluoromethoxyphenyl)cyclohexyl)cyclohexyl)-2Z,4-pentadiene

EXAMPLE 7

Preparation of 1-(4-(4-cyanophenyl)cyclohexyl)-3E,5-hexadiene

Tetrahydrofuran (100 ml) was added to 2-(1,3-dioxan-2-yl)ethyltriphenylphosphonium bromide (19.2 g, 42 mmols), followed by suspending, stirring under ice cooling till the liquid temperature reached 10° C. The reaction mixture was added potassium t-butoxide (4.7 g, 42 mmols), followed by elevating the temperature up to room temperature under ice cooling for one hour, stirring for one hour, dropwise adding a tetrahydrofuran (20 ml) solution of 2-(4-(4-cyanophenyl) cyclohexyl)acetaldehyde (9.0 g, 40 mmols) over 30 minutes from the dropping funnel, further stirring the reaction mixture for 5 hours after completion of the dropwise addition, adding ether (100 ml), allowing to stand for one hour, filtering off deposited insoluble substance, concentrating the filtrate under reduced pressure and isolating and purifying the resulting pale brown oil by means of silica gel column chromatography, to obtain white solids (6.8 g, 20 mmols) of 1-(4-(1,3-dioxan-2-yl)-2-butenyl)-4-(4-cyanophenyl)cyclohexane.

The thus obtained cyclohexane derivative was dissolved in a mixed solvent of acetone (100 ml) with 2N hydrochloric acid (10 ml), followed by heating the solution under reflux for 4 hours, cooling the reaction mixture down to room temperature after completion of the stirring, adding water, extracting with ether (100 ml), drying the resulting organic layer over anhydrous magnesium sulfate, and concentrating under reduced pressure to obtain 5-(4-(4-cyanophenyl)cyclohexyl)- 2E-pentenal (2.7 g, 10 mmols). This product was used in the subsequent reaction without any purification.

Methyltriphenylphosphonium bromide (2.7 g, 7.5 mmols) was dissolved in tetrahydrofuran (50 ml), followed by adding potassium t-butoxide (850 mg, 7.5 mmols) while stirring the solution under ice cooling, further elevating the temperature up to room temperature under ice cooling, stirring for one hour, dropwise adding to the reaction mixture, tetrahydrofuran (10 ml) solution of the above-obtained 5-(4-(4-cyanophenyl)cyclohexyl)-2E-pentenal (1.7 g, 6.3 mmols), further stirring the reaction mixture for 5 hours after completion of the dropwise addition, adding ether (50 ml), allowing to stand for one hour, filtering off deposited insoluble substance, concentrating the filtrate under reduced pressure, isolating and purifying the resulting pale brown oil by means of silica gel column chromatography and recrystallizing from ethanol, to obtain a pure, captioned compound (760 mg, 2.8 mmols). The phase transition temperature of this compound is as follows:

C—N 68.0 N—I 96.5° C.

In the same manner as the above, the following compounds are prepared:

1-(4-(4-fluorophenyl)cyclohexyl)-3E,5-hexadiene 1-(4-(4(4-fluorophenyl) cyclohexyl)cyclohexyl)-cyclohexyl)-3E,5-hexadiene 1-(4-(4-(4-fluorophenyl)phenyl)cyclohexyl)-3E,5-hexadiene 1-(4-(4-ethylphenyl)cyclohexyl)-3E,5-hexadiene 1-(4-(4-(4-ethylphenyl)cyclohexyl)cyclohexyl)-3E,5-hexadiene 1-(4-(4-(4-ethylphenyl)phenyl)cyclohexyl)-3E,5-hexadiene 1-(4-(4-propylphenyl)cyclohexyl)-3E,5-hexadiene 1-(4-(4-(4-propylphenyl)cyclohexyl)cyclohexyl)-3E,5-hexadiene 1-(4-(4-(4-propylphenyl)phenyl)cyclohexyl)-3E,5-hexadiene 1-(4-(4-pentylphenyl)cyclohexyl)-3E,5-hexadiene 1-(4-(4-(4 -pentylphenyl)cyclohexyl)cyclohexyl-3E,5-hexadiene 1-(4-(4-(4-pentylphenyl)phenyl)cyclohexyl)-3E,5-hexadiene 1-(4-(4_-(3,4-difluorophenyl)cyclohexyl)cyclohexyl)-3E,5-hexadiene 1-(4-(4-(3,4-difluorophenyl)phenyl)cyclohexyl)-3E,5-hexadiene 1-(4-(4-trifluoromethylphenyl)cyclohexyl)-3E,5-hexadiene 1-(4-(4-(4-trifluoromethylphenyl)cyclohexyl)cyclohexyl)-3E,5-hexadiene 1-(4-(4-(4-trifluoromethylphenyl)phenyl)cyclohexyl)-3E,5-hexadiene 1-(4-(3-fluoro-4-trifluoromethylphenyl)cyclohexyl)-3E,5-hexadiene 1-(4-(4-(3-fluoro-4-trifluoromethylphenyl)cyclohexyl)cyclohexyl)-3E,5-hexadiene 1-(4-(4-(3-fluoro-4-trifluoromethylphenyl)phenyl)-cyclohexyl)-3E,5-hexadiene 1-(4-(4-trifluoromethoxyphenyl)cyclohexyl)-3E,5-hexadiene 1-(4-(4-(4-trifluoromethoxyphenyl)cyclohexyl)cyclohexyl)-3E,5-hexadiene 1-(4-(4-(4-trifluoromethoxyphenyl)phenyl)cyclohexyl)-3E,5-hexadiene 1-(4-(3-fluoro-4-trifluoromethoxyphenyl)cyclohexyl)-3E,5-hexadiene 1-(4-(4-(3-fluoro-4-trifluoromethoxyphenyl)cyclohexyl)cyclohexyl)-3E, 5-hexadiene 1-(4-(4-(3-fluoro-4-trifluoromethoxyphenyl)phenyl)-cyclohexyl)-3E,5-hexadiene 1-(4-(3,5-difluoro-4-trifluoromethoxyphenyl)cyclohexyl)-3E,5-hexadiene 1-(4-(4-(3,5-difluoro-4-trifluoromethoxyphenyl)-cyclohexyl)cyclohexyl)-3E,5-hexadiene 1-(4-(4-(3,5-difluoro-4-trifluoromethoxyphenyl)-phenyl)cyclohexyl)-3E,5-hexadiene 1-(4-(3,4,5-trifluorophenyl)cyclohexyl)-3E,5-hexadiene 1-(4-(4-(3,4,5-trifluorophenyl)cyclohexyl)cyclohexyl)-3E,5-hexadiene 1-(4-(4-(3,4,5-trifluorophenyl)phenyl)cyclohexyl)-3E,5-hexadiene

EXAMPLE 8

Preparation of 1-(4-(4-cyanophenyl)cyclohexyl)-4-methyl-1E,3-pentadiene

Isopropyltriphenylphosphonium iodide (2.2 g, 5 mmols) was dissolved in tetrahydrofuran (5 ml), followed by adding potassium t-butoxide (561 mg, 5 mmols) while stirring the solution under ice cooling, further elevating the temperature up to room temperature under ice cooling for one hour, stirring for one hour, dropwise adding to the reaction mixture, a tetrahydrofuran (1 ml) solution of 3-(4-(4-cyanophenyl)cyclohexyl)-2E-propenal (800 mg, 3.3 mmols) obtained according to the process described in Example 1, further stirring the reaction mixture for 5 hours after completion of the dropwise addition, adding ether (20 ml), allowing to stand for one hour, filtering off deposited insoluble substance, concentrating the filtrate under reduced pressure, isolating and purifying the resulting pale brown oil by means of silica gel column chromatography and recrystallizing from ethanol, to obtain a pure, captioned compound (440 mg, 1.7 mmol). The phase transition points of this compound are shown below.

C—I 80.5 (N—I 69.3) °C.

In the same manner as the above, the following compounds are obtained:

1-(4-(4-cyanophenyl)cyclohexyl)-4-methyl-1E,3E-hexadiene 1-(4-(4-cyanophenyl)cyclohexyl)-4-methyl-1E,3E-heptadiene 1-(4-(4-fluorophenyl)cyclohexyl)-4-methyl-1E,3-pentadiene 1(4-(4-(4-fluorophenyl)cyclohexyl)cyclohexyl-4-methyl-1E,3-pentadiene 1-(4-(3,4-difluorophenyl)cyclohexyl)-4-methyl-1E,3-pentadiene 1-(4-(4-(3,4-difluorophenyl)cyclohexyl)cyclohexyl)-4-methyl-1E,3-pentadiene 1-(4-(3,4,5-trifluorophenyl)cyclohexyl)-4-methyl-1E,3-pentadiene 1-(4-(4-(3,4,5-trifluorophenyl)cyclohexyl)cyclohexyl)-4-methyl-1E,3-pentadiene 1-(4-(4-ethylphenyl)cyclohexyl)-4-methyl-1E,3-pentadiene 1-(4-(4-(4-ethylphenyl)cyclohexyl)cyclohexyl)-4-methyl-1E,3-pentadiene 1-(4-(4-propylphenyl)cyclohexyl)-4-methyl-1E,3-pentadiene 1-(4-(4-(4-propylphenyl)cyclohexyl)cyclohexyl)-4-methyl-1E,3-pentadiene 1-(4-(4-pentylphenyl)cyclohexyl)-4-methyl-1E,3-pentadiene 1-(4-(4-(4-pentylphenyl)cyclohexyl)cyclohexyl)-4-methyl-1E,3-pentadiene 1-(4-(4-trifluoromethylphenyl)cyclohexyl)-4-methyl-1E,3-pentadiene 1-(4-(4-(4-trifluoromethylphenyl)cyclohexyl)cyclohexyl)-4-methyl-1E,3-pentadiene 1-(4-(3-fluoro-4-trifluoromethylphenyl)cyclohexyl)-4-methyl-1E,3-pentadiene 1-(4-(4-(4-trifluoromethoxyphenyl)cyclo-
   hexyl)cyclohexyl)-4-methyl-1E,3-pentadiene 1-(4-(3-fluoro-4-trifluoromethoxyphenyl)cyclohexyl)-4-
   methyl-1E,3-pentadiene 1-(4-(4-(3-fluoro-4-trifluoromethoxyphenyl)cyclo-
   hexyl)cyclohexyl)-2-methyl-1E,3-pentadiene 1-(4-(3,5-difluoro-4-trifluoromethylphenyl)cyclohexyl)-
   4-methyl-1E,3-pentadiene 1-(4-(4-(3,5-difluoro-4-trifluoromethylphenyl)cyclo-
   hexyl)cyclohexyl)-4-methyl-1E,3-pentadiene

EXAMPLE 9

Preparation of 1-(4-(4-cyanophenyl)cyclohexyl)-1E,
3E-pentadiene

Chromium chloride (II) (5.0 g, 40 mmols) was placed in a vessel purged with argon, followed by adding tetrahydrofuran (100 ml), stirring the mixture under a heterogensous condition, adding 1,1-diiodoethane (2.8 g, 10 mmols) and a tetrahydrofuran (10 ml) solution of 3-(4-(4-cyanophenyl)cyclohexyl)-2E-propenal (1.2 g, 5 mmols) obtained according to a process described in Example 1, while stirring the suspension at room temperature, stirring at room temperature for 16 hours. The resulting mixture was poured into water after completion of the reaction, followed by extracting with heptane (50 ml), washing the resulting organic layer with water, drying over anhydrous magnesium sulfate, concentrating under reduced pressure, isolating and purifying the resulting pale yellow oil by means of silica gel column chromatography and recrystallyzing the resulting colorless oil from ethanol, to obtain a pure, captioned compound (380 mg, 1.5 mmol). The phase transition temperature of this compound is shown below.

C—N 74.4° C. N—I 147.2° C.

In the same manner as the above, the following compounds are prepared:

1-(4-(4-cyanophenyl)cyclohexyl)-1E,3E -hexadiene 1-(4-(4-cyanophenyl)cyclohexyl)-1E,3E -heptadiene 1-(4-(4-fluorophenyl)cyclohexyl)-1E,3E -pentadiene 1-(4-(4-(4-fluorophenyl)cyclohexyl)cyclohexyl)-1E,3E-
   pentadiene 1-(4-(4-fluorophenyl)cyclohexyl)-1,E3E -hexadiene 1-(4-(3,4-difluorophenyl)cyclohexyl)-1E,3E -pentadiene 1-(4-(4-(3,4-difluorophenyl)cyclohexyl)cyclohexyl) -1E,
   3E-pentadiene 1-(4-(3,4-difluorophenyl)cyclohexyl)-1E,3E -hexadiene 1-(4-(4-ethylphenyl)cyclohexyl)-1E,3E -pentadiene 1-(4-(4-(4-ethylphenyl)cyclohexyl)cyclohexyl) -1E,3E-
   pentadiene 1-(4-(4-ethylphenyl)cyclohexyl)-1E,3E -hexadiene 1-(4-(4-propylphenyl)cyclohexyl)-1E,3E -pentadiene 1-(4-(4-(4-propylphenyl)cyclohexyl)cyclohexyl)-1E,3E-
   pentadiene 1-(4-(4-propylphenyl)cyclohexyl)-1E,3E -hexadiene 1-(4-(4-pentylphenyl)cyclohexyl)-1E,3E -pentadiene 1-(4-(4-(4-pentylphenyl)cyclohexyl)cyclohexyl) -1E,3E-
   pentadiene 1-(4-(4-butylphenyl)cyclohexyl)-1E,3E -hexadiene 1-(4-(4-trifluoromethylphenyl)cyclohexyl)-1E,3E-pentadiene 1-(4-(4-(4-trifluoromethylphenyl)cyclohexyl) -cyclohexyl)-1E,3E-pentadiene 1-(4-(4-(4-trifluoromethylphenyl)cyclohexyl)-3E, 5E-hexadiene 1-(4-(4-trifluoromethoxyphenyl)cyclohexyl)-1E,3E-pentadiene 1-(4-(4-4-trifluoromethoxyphenyl)cyclo-
   hexyl)cyclohexyl)-1E,3E-pentadiene 1-(4-(4-trifluoromethoxyphenyl)cyclohexyl)-1E,
   3E-hexadiene 1-(4-(3-fluoro-4-trifluoromethylphenyl)cyclohexyl)-1E,
   3E-pentadiene 1-(4-(4-(3-fluoro-4-trifluoromethylphenyl)cyclo-
   hexyl)cyclohexyl)-1E,3E-pentadiene 1-(4-(3-fluoro-4-trifluoromethylphenyl)cyclohexyl)-1E,
   3E-hexadiene 1-(4-(3-fluoro-4-trifluoromethoxyphenyl)cyclohexyl)-
   1E,3E-pentadiene 1-(4-(4-(3-fluoro-4-trifluoromethoxy-phenyl)cyclohexyl)
   cyclohexyl)-1E,3E-pentadiene 1-(4-(3-fluoro-4-trifluoromethoxyphenyl)cyclohexyl)-
   1E,3E-hexadiene 1-(4-(3,5-difluoro-4-trifluoromethoxyphenyl)cyclo-
   hexyl)-1E,3E-hexadiene 1-(4-(4-(3,5-difluoro-4-trifluoromethyl-phenyl)cyclo-
   hexyl)cyclohexyl)-1E,3E-pentadiene 1-(4-(3,5-difluoro-4-trifluoromethylphenyl)-cyclohexyl)-
   1E,3E-hexadiene 1-(4-(3,5-difluoro-4-trifluoromethoxyphenyl)cyclo-
   hexyl)-1E,3E-pentadiene 1-(4-(4-(3,5-difluoro-4-trifluoromethoxy-phenyl)cyclo-
   hexyl)cyclohexyl)-1E,3E-pentadiene 1-(4-(3,5-difluoro-4-trifluoromethoxyphenyl)cyclo-
   hexyl)-1E,3E-hexadiene 1-(4-(3,4,5-trifluorophenyl)cyclohexyl)-1E,3E-pentadiene 1-(4-(4-(3,4,5-trifluorophenyl)cyclohexyl)cyclohexyl)-
   1E,3E-pentadiene 1-(4-(3,4,5-trifluorophenyl)cyclohexyl)-1E,3E-hexadiene

EXAMPLE 10

Preparation of 1-(4-(4-propylcyclohexyl)cyclohexyl)-1E,3-butadiene

Into a three-necked flask equipped with a dropping funnel, a three-way cock and a thermometer was placed (2-(1, 3-dioxan-2-yl)ethyl)triphenylphosphonium bromide (12.3 g, 27 mmols), followed by adding tetrahydrofuran (50 ml), suspending, stirring under ice cooling till the liquid temperature reached 10° C. The reaction mixture is added potassium t-butoxide (3.0 g, 27 mmols), followed by elevating the temperature up to room temperature under ice cooling for one hour, stirring for one hour, dropwise adding a tetrahydrofuran (10 ml) solution of 4-(4-propylcyclohexyl) cyclohexanone (15.6 g, 25 mmols) over 30 minutes from the dropping funnel, further stirring the reaction mixture for 5 hours after completion of the dropwise addition, adding ether (50 ml), allowing to stand for one hour, filtering off deposited insoluble substance, concentrating the filtrate under reduced pressure, isolating and purifying the resulting pale brown oily substance by means of silica gel column chromatography and recrystallizing from ethanol, to obtain 1-(2-(1,3-dioxan-2-yl)ethylidene)-4-(4-propylcyclohexyl) cyclohexane (4.5 g, 14 mmols).

The resulting cyclohexane derivative was dissolved in a mixed solvent of acetone (80 ml) with 2N hydrochloric acid (8 ml), followed by heating the solution under reflux for 4 hours, cooling the reaction mixture down to room temperature after completion of the stirring, adding water, extracting with ether (50 ml), drying the organic layer over anhydrous magnesium sulfate, and concentrating under reduced pressure to obtain 3-(4-(4-propylcyclohexyl)cyclohexyl)-2E-propenal (3.1 g, 12 mmols). This product was used in the subsequent reaction without any purification.

Methyltriphenylphosphonium bromide (5.2 g, 14 mmols) was dissolved in tetrahydrofuran, followed by adding potassium t-butoxide (1.6 g, 14 mmols), further elevating the temperature up to room temperature under ice cooling for one hour, stirring for one hour, dropwise adding to the reaction mixture, a tetrahydrofuran (5 ml) solution of the above-obtained 3-(4-(4-propylcyclohexyl)cyclohexyl)-2E-propenal (3.1 g, 12 mmols), further stirring the reaction mixture for 5 hours after completion of the dropwise addition, adding ether (50 ml), allowing to stand for one hour, filtering off deposited insoluble substance, concentrating the filtrate under reduced pressure, isolating and purifying the resulting pale brown oily substance by way of silica gel column chromatography and recrystallizing to obtain the captioned compound (321 mg, 1.2 mmol).

In the same manner as the above, the following compounds are prepared;

1-(4-(4-ethylcyclohexyl)cyclohexyl)1E,3-butadiene
1-(4-(4-pentylcyclohexyl)cyclohexyl)-1E,3-butadiene
1-(4-(4-ethoxycyclohexyl)cyclohexyl)-1E,3-butadiene
1-(4-(4-propoxycyclohexyl)cyclohexyl)-1E,3-butadiene
1-(4-(4-pentyloxycyclohexyl)cyclohexyl)-1E,3-butadiene
1-(4-(4-trifluoromethylcyclohexyl)cyclohexyl)-1E,3-butadiene
1-(4-(4-trichloromethylcyclohexyl)cyclohexyl)-1E,3-butadiene
1-(4-(4-trifluoromethoxycyclohexyl)cyclohexyl)-1E,3-butadiene
1-(4-(4-ethylcyclohexyl)cyclohexyl)-3E,5-hexadiene
1-(4-(4-pentylcyclohexyl)cyclohexyl)-3E,5-hexadiene
1-(4-(4-ethoxycyclohexyl)cyclohexyl)-3E,5-hexadiene
1-(4-(4-propoxycyclohexyl)cyclohexyl)-3E,5-hexadiene
1-(4-(4-pentyloxycyclohexyl)cyclohexyl)-3E,5-hexadiene
1-(4-(4-trifluoromethylcyclohexyl)cyclohexyl)-3E,5-hexadiene
1-(4-(4-trichloromethylcyclohexyl)cyclohexyl)-3E,5-hexadiene
1-(4-(4-trifluoromethoxycyclohexyl)cyclohexyl)-3E,5-hexadiene

EXAMPLE 11

(Use example 1)

1-(4-(4-Cyanophenyl)cyclohexyl)-1E,3-butadiene of the compound of the present invention (15%) was mixed with a liquid crystal composition, ZLI-1132 made by Merck Co., Ltd. consisting of

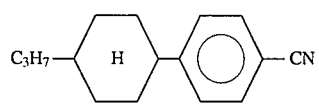 24 parts by weight

C$_5$H$_{11}$—H—◯—CN    36 parts by weight,

C$_7$H$_{15}$—H—◯—CN    25 parts by weight and

C$_5$H$_{11}$—H—◯—◯—CN    15 parts by weight, and the values of physical properties of the resulting composition were measured. The results were as follows:

Cp (°C.)=95.7, $\Delta\epsilon$=15.0, $\Delta n$=0.210, $\eta_{20}$=40.3,
Vth (V)=1.61, and $K_{33}/K_{11}$=2.36.

Further, when this composition was allowed to stand in a freezer at −20° C. for 20 days, no deposition of crystals was observed.

EXAMPLE 12

(Use example 2)

1-(4-(4-Cyanophenyl)cyclohexyl)-3E,5-hexadiene of the compound of the present invention (15%) was mixed with the above-mentioned ZLI-1132, and the values of the physical properties of the resulting composition were measured. The results were as follows:

Cp (°C.)=104.4, $\Delta\epsilon$=13.7, $\Delta n$=0.190,
$\eta_{20}$=41.0, Vth (V)=1.74, $K_{33}/K_{11}$=2.31.

Further, when this composition was allowed to stand in a freezer at −20° C. for 20 days, no deposition of crystals was observed.

EXAMPLE 13

(Use example 3)

1-(4-(4-Propylcyclohexyl)cyclohexyl)-1E,3-butadiene of the compound of the present invention (2%) was mixed with the above-mentioned ZLI-1132, and the values of the physical properties of the resulting composition were measured. The results were as follows:

Cp (°C.)=69.3, $\Delta\epsilon$=9.0, $\Delta n$=0.134, $\eta_{20}$=27.4,
Vth (V)=1.61, $K_{33}/K_{11}$=2.09.

Further, when this composition was allowed to stand in a freezer at −30° C. for 20 days, no deposition of crystals was observed.

EXAMPLE 14

(Use example 4)

1-(4-(4-Fluorophenyl)cyclohexyl)-1E,3-butadiene of the compound of the present invention (15%) was mixed with the above-mentioned ZLI-1132, and the values of the physical properties of the resulting composition were measured. The results were as follows:

Cp (°C.)=59.0, $\Delta\epsilon$=8.5, $\Delta n$=0.129, $\eta_{20}$=21.6,
Vth (V)=1.44 and $K_{33}/K_{11}$=2.05.

When this composition was allowed to stand in a freezer at −20° C. for 20 days, no deposition of crystals was observed.

(Effectiveness of the Invention)

The compound of the present invention is a novel liquid crystalline compound having a carbon chain containing a conjugated double bond at the terminal part of the molecule, and can provide a liquid crystal material having characteristics having not been obtained so far. In STN mode the use of which is now increasing in a liquid crystal display, an important characteristic of liquid crystal materials is a ratio of elastic constants of bending and expansion ($K_{33}/K_{11}$). Since the compound of the present invention has a large value of $K_{33}/K_{11}$, the steepness in a device increases to give a clear pictorial image. Further, the compound of the present invention has a relatively low viscosity and exhibits a higher NI point than those of existing similar compounds.

What we claim is:

1. A diene derivative expressed by the formula (I)

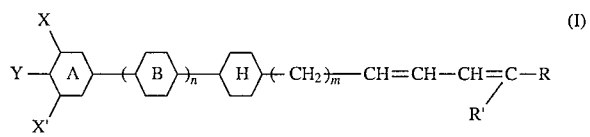

wherein R and R' each independently represent a hydrogen atom or an alkyl group of 1 to 5 carbon atoms; A represents 1,4-phenylene and B represents 1,4-cyclohexylene or 1,4-phenylene; n represents 0 or 1; m represents an integer of 0 to 2; X and X' each independently represent a hydrogen atom or a fluorine atom and Y represents an alkyl group of 1 to 5 carbon atoms, a halogen atom, a cyano group, an alkoxy group of 1 to 5 carbon atoms, a methyl group substituted by 1 to 3 halogen atoms or a trihaloalkoxy group of 1 to 5 carbon atoms and R and R' do not represent simultaneously an alkyl group of 4 or more carbon atoms.

2. A diene derivative according to claim 1, wherein Y represents a fluorine atom; n represents 0; and R and R' each represent a hydrogen atom.

3. A diene derivative according to claim 1, wherein Y represents an alkyl group of 1 to 5 carbon atoms, an alkoxy group of 1 to 5 carbon atoms, a trifluoromethyl group or a trifluoromethoxy group; and n represents 0.

4. A diene derivative according to claim 1, wherein Y represents a fluorine atom or an alkyl group of 1 to 5 carbon atoms; m represents 1 or 2; and R and R' each represent a hydrogen atom.

5. A diene derivative according to claim 1, wherein Y represents an alkoxy group of 1 to 5 carbon atoms, a trifluoromethyl group or a trifluoromethoxy group; m represents 1 or 2; and R and R' each represent hydrogen atom.

6. A liquid crystal composition comprising at least two components at least one of which is a diene derivative as set forth in claim 1.

7. A diene derivative according to claim 1, wherein B represents 1,4-cyclohexylene; Y represents a fluorine atom; n represents 1; and R and R' each represent a hydrogen atom.

* * * * *